United States Patent
Gabriel et al.

(10) Patent No.: US 7,645,764 B2
(45) Date of Patent: Jan. 12, 2010

(54) KINASE INHIBITORS AND METHODS FOR USING THE SAME

(75) Inventors: Tobias Gabriel, San Francisco, CA (US); Joel McIntosh, Pacifica, CA (US); Kin-Chun Thomas Luk, North Caldwell, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 9 days.

(21) Appl. No.: 11/983,313

(22) Filed: Nov. 8, 2007

(65) Prior Publication Data

US 2008/0132528 A1 Jun. 5, 2008

Related U.S. Application Data

(60) Provisional application No. 60/858,203, filed on Nov. 9, 2006.

(51) Int. Cl.
*A61K 31/519* (2006.01)
*C07D 471/04* (2006.01)
*C07D 487/04* (2006.01)
*C07D 239/28* (2006.01)
*C07D 271/10* (2006.01)
*C07D 413/14* (2006.01)
*C07C 69/78* (2006.01)
*C07D 241/02* (2006.01)
*C07D 243/10* (2006.01)
*A61P 35/00* (2006.01)
*A61P 17/06* (2006.01)

(52) U.S. Cl. .............. 514/264.11; 544/279; 544/407; 548/143; 560/60; 560/103; 564/149

(58) Field of Classification Search ............ 544/279; 514/264.11
See application file for complete search history.

(56) References Cited

U.S. PATENT DOCUMENTS

| | | | |
|---|---|---|---|
| 4,271,164 A | 6/1981 | Blankley et al. | |
| 5,338,740 A | 8/1994 | Carpino et al. | |
| 5,620,981 A | 4/1997 | Blankley et al. | |
| 5,733,913 A | 3/1998 | Blankley et al. | |
| 5,733,914 A | 3/1998 | Blankley et al. | |
| 5,952,342 A | 9/1999 | Blankley et al. | |
| 6,150,359 A | 11/2000 | Barvian et al. | |
| 6,498,163 B1 | 12/2002 | Boschelli et al. | |
| 6,936,612 B2 | 8/2005 | Barvian et al. | |
| 2002/0137756 A1 | 9/2002 | Chen et al. | |
| 2003/0073668 A1 | 4/2003 | Booth et al. | |
| 2003/0220345 A1 | 11/2003 | Hamby et al. | |
| 2004/0019210 A1 | 1/2004 | Chivikas et al. | |
| 2005/0137214 A1 | 6/2005 | Barvian et al. | |
| 2005/0182078 A1 | 8/2005 | Barvian et al. | |
| 2005/0187230 A1 | 8/2005 | Ding et al. | |

FOREIGN PATENT DOCUMENTS

| | | |
|---|---|---|
| WO | WO 9937643 A1 | 7/1999 |
| WO | WO 02/18379 A2 | 3/2002 |
| WO | WO 02/18380 A1 | 3/2002 |
| WO | WO 02/28853 A1 | 4/2002 |
| WO | WO 2005/034869 A2 | 4/2005 |
| WO | WO 2005/073189 A1 | 8/2005 |
| WO | WO 2005/073217 A1 | 8/2005 |
| WO | WO 2005/073219 A1 | 8/2005 |
| WO | WO 2005/073232 A1 | 8/2005 |
| WO | WO 2007136465 * | 5/2006 |

* cited by examiner

*Primary Examiner*—James O Wilson
*Assistant Examiner*—Cecilia M Jaisle
(74) *Attorney, Agent, or Firm*—Robert C. Hall

(57) ABSTRACT

Compounds of formula I:

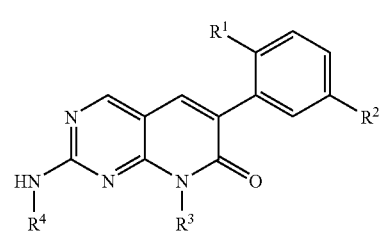

wherein $R^1$, $R^2$, $R^3$ and $R^4$ are as defined herein. Also disclosed are methods of making the compounds, pharmaceutical compositions, methods of using the compounds for treatment of p38 MAP kinase-mediated diseases, and methods of using the compounds for treatment of Raf kinase-mediated diseases.

16 Claims, No Drawings

KINASE INHIBITORS AND METHODS FOR USING THE SAME

CROSS REFERENCE TO RELATED APPLICATIONS

This application claims the benefit of priority of U.S. Provisional Patent Application Ser. No. 60/858,203 filed Nov. 9, 2006, the disclosure of which is incorporated herein by reference in its entirety.

FIELD OF THE INVENTION

The present invention relates to fused pyrimido-pyridone derivatives and related compounds, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The role of p38 MAP kinase as a therapeutic target in oncology has been reviewed: Podar, K. H.; Teru; Chauhan, Dharminder; Anderson, Kenneth C., "Targeting signalling pathways for the treatment of multiple myeloma", *Expert Opinion on therapeutic Targets* 2005, 9, 359-381; Schultz, R. M., "Potential of p38 MAP kinase inhibitors in the treatment of cancer", *Progress in Drug Research* 2003, 60, 59-92.

The inhibition of these cytokines by inhibition of the p38 kinase is of benefit in controlling, reducing and alleviating many of these disease states.

Many disease states are characterized by uncontrolled proliferation and differentiation of cells. These disease states encompass a variety of cell types and maladies such as cancer, atherosclerosis, and restenosis. In many such disease states kinases, important cellular enzymes that perform essential functions by regulating cell division and proliferation, appear to play a decisive role.

The molecular mechanisms and signaling pathways that regulate cell proliferation and survival are now receiving attention as potential targets for anticancer strategies. Recently, increased efforts have been directed at targeting the MAPK pathway, which integrates a wide array of proliferative signals initiated by receptor tyrosine kinases (RTKs) and G protein-coupled receptors.

The MAPK signal cascade includes the G protein Ras, which works at the upstream end of a core module consisting of 3 kinases: Raf, MEK1/2 and ERK1/2. Raf phosphorylates and activates MEK1/2, which in turn leads to the activation of ERK1/2. Raf kinase has long been considered an attractive target for drug discovery due to its importance as a potential checkpoint for cancer-related signal transduction (Strumberg and Seeber, Onkologie, 2005, 28: 101-107; Beeram et al., J. Clin. Oncol. 2005, 23: 6771-6790).

The importance of the MAPK signalling cascade for the proliferation and survival of tumor cells recently increased with the discovery of activating B-Raf mutations in human tumors. Activating Raf mutations have been identified in melanoma, thyroid, colon, and other cancers (Strumberg and Seeber, Onkologie, 2005, 28: 101-107; Bollag et al., Current Opinion in Investigational Drugs, 2003, 4:1436-1441). Thus, in addition to a role in controlling tumors with Ras mutations and activated growth factor receptors, inhibitors of Raf kinase may harbor therapeutic potential in tumors carrying a B-Raf oncogene (Sharma et al., Cancer Res. 2005, 65: 2412-2421).

The mammalian Raf serine/threonine kinase family consists of three 68- to 74-kd proteins termed A-Raf, B-Raf, and C-Raf (Raf-1), which share highly conserved amino-terminal regulatory regions and catalytic domains at the carboxyl terminus. Raf proteins are normally cytosolic but are recruited to the plasma membrane by the small G-protein Ras, which is an essential step for their activation by growth factors, cytokines, and hormones. At the membrane, Raf activation occurs through a highly complex process involving conformation changes, binding to other proteins, binding to lipids, and phosphorylation and dephosphorylation of some residues.

A variety of agents have been discovered that modulate Raf kinase, including antisense oligonucleotides and small molecules. These inhibitors prevent the expression of Raf protein, block Ras/Raf interaction, or obstruct its kinase activity. Down regulation of B-Raf activity by siRNA or through the kinase inhibitors leads to inhibition of the growth of melanoma cells and siRNA-mediated reduction of B-Raf led to decreased tumorigenic potential of 1205 Lu cells. Raf inhibitors currently undergoing clinical evaluation show promising signs of anti-cancer efficacy with a very tolerable safety profile.

Despite the progress that has been made, the search continues for low molecular weight compounds that are useful for treating a wide variety of tumors and other proliferative disorders including restenosis, angiogenesis, diabetic retinopathy, psoriasis, surgical adhesions, macular degeneration, and atherosclerosis. Thus, a strong need exists to provide compositions, pharmaceuticals and/or medicaments with anti-proliferative activity. Such compositions, pharmaceuticals and/or medicaments may possess not only strong activity, but also exert diminished side effects in comparison to other anti-proliferative agents. Furthermore, the spectrum of tumors responsive to treatment with such compositions, pharmaceuticals and/or medicaments may be broad. Active ingredients of this type may be suitable in the mentioned indication as single agent, and/or in combination therapy, be it in connection with other therapeutic agents, with radiation, with operative/surgical procedures, heat treatment or any other treatment known in the mentioned indications.

SUMMARY

The invention provides compounds of formula I:

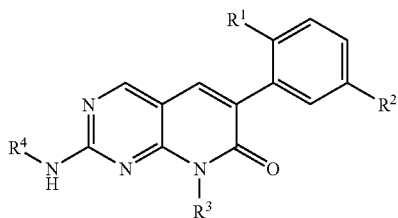

or a pharmaceutically acceptable salt thereof, wherein:
$R^1$ is:
  $C_{1-6}$alkyl;
  halo;
  $C_{1-6}$alkoxy;
  halo-$C_{1-6}$alkyl; or
  hetero-$C_{1-6}$alkyl;
$R^2$ is:
  cyano;
  an optionally substituted five membered monocyclic heteroaryl;
  —C(O)—$OR^a$;
  —C(O)—$NR^bR^c$; or
  —C(O)—$NR^d$—$NR^e$—$R^f$;
  wherein
    $R^a$, $R^b$, $R^d$ and $R^e$ each independently is:
      hydrogen; or
      $C_{1-6}$alkyl; and
    $R^c$ and $R^f$ each independently is:
      hydrogen;
      $C_{1-6}$alkyl;
      halo-$C_{1-6}$alkyl;
      $C_{1-6}$alkoxy;
      hetero-$C_{1-6}$alkyl;
      $C_{3-6}$cycloalkyl;
      $C_{3-6}$cycloalkyl-$C_{1-6}$alkyl;
      aryl;
      aryl-$C_{1-6}$alkyl;
      heteroaryl; or
      heteroaryl-$C_{1-6}$alkyl;
      $C_{1-6}$alkyl-carbonyl;
      halo-$C_{1-6}$alkyl-carbonyl;
      aryl-carbonyl;
      aryl-$C_{1-6}$alkyl-carbonyl;
      heteroaryl-carbonyl; or
      heteoraryl-$C_{1-6}$alkyl-carbonyl.
$R^3$ is:
  $C_{1-6}$alkyl;
  $C_{3-6}$cycloalkyl;
  $C_{3-6}$cycloalkyl-$C_{1-6}$alkyl; or
  hetero-$C_{1-6}$alkyl; and $R^4$ is:
  $C_{1-6}$alkyl;
  halo-$C_{1-6}$alkyl;
  hetero-$C_{1-6}$alkyl;
  $C_{3-6}$cycloalkyl;
  $C_{3-6}$cycloalkyl-$C_{1-6}$alkyl;
  aryl;
  aryl-$C_{1-6}$alkyl;
  heteroaryl;
  heteroaryl-$C_{1-6}$alkyl;
  heterocyclyl; or
  heterocyclyl-$C_{1-6}$alkyl.

Another aspect of the invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective for p38 kinases, Raf kinases and receptor tyrosine kinases like VEGFR2, and PDGFR relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, methanesulfonylpropyl, and the like.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkylsulfinyl" means a moiety of the formula —S(O)R wherein R is alkyl as defined herein.

"Alkylsulfonyl" means a moiety of the formula —SO$_2$R wherein R is alkyl as defined herein.

"Alkylcarbonyl" means a group —C(O)—R wherein R is alkyl as defined herein.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Arylcarbonyl" means a group —C(O)—R wherein R is aryl as defined herein.

"Aralkyl" or "arylalkyl", which may be used interchangeably, refers to a moiety of the formula Ar$^a$—R$^z$—, where Ara is optionally substituted aryl and R$^z$ is alkylene as defined herein.

"Aralkylcarbonyl" and "arylalkylcarbonyl" mean a group —C(O)—R wherein R is aralkyl or arylalkyl as defined herein.

"Acyl" means a group of the formula —C(O)—R, —C(O)—OR or —C(O)—NRR' wherein R is hydrogen, alkyl, haloalkyl, heteroalkyl or amino as defined herein, and R' is hydrogen or alkyl as defined herein.

"Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula R$^c$—R$^d$—, where R$^c$ is cycloalkyl and R$^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Haloalkylcarbonyl" means a group —C(O)—R wherein R is haloalkyl as defined herein.

"Heteroalkyl" means an alkyl moiety as defined herein wherein one or more, preferably one, two or three, hydrogen atoms have been replaced with a substituent independently selected from the group consisting of —OR$^a$, —NR$^b$R$^c$ and —S(O)$_n$R$^d$ (where n is an integer from 0 to 2), with the understanding that the point of attachment of the heteroalkyl moiety is through a carbon atom, wherein R$^a$ is hydrogen, acyl, alkoxycarbonyl, alkyl, hydroxyalkyl, alkoxyalkyl, alkylsulfonyl, aminocarbonyl, aminosulfonylamino, cycloalkyl, or cycloalkylalkyl; R$^b$ and R$^c$ are independently of each other hydrogen, acyl, alkoxycarbonyl, aminocarbonyl, aminocarbonyl, aminosulfonylamino, hydroxyalkyl, alkoxyalkyl, alkylsulfonyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, R$^d$ is hydrogen, alkyl, cycloalkyl, cycloalkylalkyl, or aryl, and when n is 1 or 2, R$^d$ is alkyl, cycloalkyl, cycloalkylalkyl, hydroxyalkyl, alkoxyalkyl, alkylamino, aminocarbonyl, aminosulfonylamino, alkylsulfonyl, amino, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]pyridinyl, imidazo[2,1-b]thiazolyl, and the derivatives thereof.

"Heteroarylalkyl" and "heteroaralkyl" refers to a moiety of the formula Ar$^z$-R$^y$—, where Ar$^z$ is heteroaryl and R$^y$ is alkylene as defined herein.

"Heteroarylcarbonyl" means a group —C(O)—R wherein R is heteroaryl as defined herein.

"Heteroarylalkylcarbonyl" and "heteroaralkylcarbonyl" means a group —C(O)—R wherein R is heteroarylalkyl or heteroaralkyl as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —$(X)_n$—C(O)$R^e$ (where X is O or $NR^f$, n is 0 or 1, $R^e$ is hydrogen, alkyl, haloalkyl, hydroxy (when n is 0), alkoxy, amino, mono- and dialkylamino, or optionally substituted phenyl, and $R^f$ is H or alkyl), -alkylene-C(O)$R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), and —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —$S(O)_nR^k$. In particular, the term heterocyclyl includes, but is not limited to, tetrahydrofuranyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'-R" wherein R is alkylene, R' is hydrogen or alkyl, and R" is hydroxyalkyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted", when used in association with "aryl", "aralkyl", "phenyl", "heteroaryl", "heteoaralkyl", "cycloalkyl" or "heterocyclyl", means an aryl, aralkyl, phenyl, heteroaryl, heteroaralkyl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —$(CR'R'')_n$—COOR (where n is an integer from 0 to 5, R' and R" are independently hydrogen or alkyl, and R is hydrogen, alkyl, cycloalkyl, cycloalkylalkyl, phenyl or phenylalkyl), or —$(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl), or as provided herein elsewhere. Some preferred optional substituents for "aryl", "aralkyl", "phenyl", "heteroaryl", "heteoaralkyl", "cycloalkyl" or "heterocyclyl" include alkyl, alkoxy, halo, haloalkyl, haloalkoxy, alkylsulfonyl, amino, nitro, cyano, acetyl and acetamidyl. More preferred are alkyl, alkoxy, halo, haloalkyl and cyano.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM® v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, the structure encompasses both enantiomers associated with the chiral center. Structures shown herein may exist in various tautomeric forms, and such structures are intended to encompass tautomers that may not be shown.

Compounds of the Invention

The invention provides compounds of formula I:

or a pharmaceutically acceptable salt thereof, wherein:

$R^1$ is:
  $C_{1-6}$alkyl;
  halo;
  $C_{1-6}$alkoxy;
  halo-$C_{1-6}$alkyl; or
  hetero-$C_{1-6}$alkyl;

$R^2$ is:
  cyano;
  an optionally substituted five membered monocyclic heteroaryl;
  —C(O)—OR$^a$;
  —C(O)—NR$^b$R$^c$; or
  —C(O)—NR$^d$—NR$^e$—R$^f$;

wherein
R$^a$, R$^b$, R$^d$ and R$^e$ each independently is:
   hydrogen; or
   C$_{1-6}$alkyl; and
R$^c$ and R$^f$ each independently is:
   hydrogen;
   C$_{1-6}$alkyl;
   halo-C$_{1-6}$alkyl;
   C$_{1-6}$alkoxy;
   hetero-C$_{1-6}$alkyl;
   C$_{3-6}$cycloalkyl;
   C$_{3-6}$cycloalkyl-C$_{1-6}$alkyl;
   aryl;
   aryl-C$_{1-6}$alkyl;
   heteroaryl; or
   heteroaryl-C$_{1-6}$alkyl;
   C$_{1-6}$alkyl-carbonyl;
   halo-C$_{1-6}$alkyl-carbonyl;
   aryl-carbonyl;
   aryl-C$_{1-6}$alkyl-carbonyl;
   heteroaryl-carbonyl; or
   heteoraryl-C$_{1-6}$alkyl-carbonyl.
R$^3$ is:
   C$_{1-6}$alkyl;
   C$_{3-6}$cycloalkyl;
   C$_{3-6}$cycloalkyl-C$_{1-6}$alkyl; or
   hetero-C$_{1-6}$alkyl; and
R$^4$ is:
   C$_{1-6}$alkyl;
   halo-C$_{1-6}$alkyl;
   hetero-C$_{1-6}$alkyl;
   C$_{3-6}$cycloalkyl;
   C$_{3-6}$cycloalkyl-C$_{1-6}$alkyl;
   aryl;
   aryl-C$_{1-6}$alkyl;
   heteroaryl;
   heteroaryl-C$_{1-6}$alkyl;
   heterocyclyl; or
   heterocyclyl-C$_{1-6}$alkyl.

In certain embodiments of formula I, R$^4$ is hetero-C$_{1-6}$alkyl or heterocyclyl.

In certain embodiments of formula I, R$^3$ is C$_{1-6}$alkyl, C$_{3-6}$cycloalkyl or hetero-C$_{1-6}$alkyl.

In certain embodiments of formula I, R$^2$ is —C(O)—NR$^a$R$^b$, —C(O)—NR$^d$—NR$^e$—R$^f$ or an optionally substituted five membered monocyclic heteroaryl.

In certain embodiments of formula I, R$^2$ is oxazolyl, thiazolyl, isoxazolyl, isothiazolyl, imidazolyl, pyrazolyl, oxadiazolyl, thiadiazolyl, triazolyl or tetrazolyl, each optionally substituted.

In certain embodiments of formula I, R$^2$ is —C(O)—NR$^b$R$^c$.

In certain embodiments of formula I, R$^2$ is —C(O)—NHR$^c$ and R$^c$ is C$_{1-6}$alkyl, C$_{1-6}$alkoxy or C$_{3-6}$cycloalkyl.

In certain embodiments of formula I, R$^2$ is —C(O)—NR$^d$—NR$^e$—R$^f$ and R$^f$ is hydrogen, C$_{1-6}$alkyl, halo-C$_{1-6}$alkyl, or aryl-C$_{1-6}$alkylcarbonyl.

In certain embodiments of formula I, R$^2$ is —C(O)—NH—NH—R$^f$ and R$^f$ is hydrogen, halo-C$_{1-6}$alkyl or aryl-C$_{1-6}$alkyl-carbonyl.

In certain embodiments of formula I, R$^2$ is —C(O)—OR$^a$.

In certain embodiments of formula I, R$^2$ is isoxazolyl, imidazolyl, oxadiazolyl or triazolyl, each optionally substituted.

In certain embodiments of formula I, R$^1$ is methyl.

In certain embodiments of formula I, R$^3$ is:
C$_{1-6}$alkyl selected from methyl, ethyl, propyl, isopropyl, n-butyl, isobutyl, tert-butyl, n-pentyl and isopentyl;

C$_{3-6}$cycloalkyl selected from cyclopropyl, cyclobutyl, cyclopentyl and cyclohexyl, each optionally substituted;

C$_{3-6}$cycloalkyl-C$_{1-6}$alkyl selected from cyclopropyl-C$_{1-6}$alkyl, cyclobutyl-C$_{1-6}$alkyl, cyclopentyl-C$_{1-6}$alkyl and cyclohexyl-C$_{1-6}$alkyl, the cycloalkyl portion of each being optionally substituted; or hetero-C$_{1-6}$alkyl selected from C$_{1-6}$alkyloxy-C$_{1-6}$alkyl, hydroxy-C$_{1-6}$alkyl, C$_{1-6}$alkylsulfanyl-C$_{1-6}$alkyl, C$_{1-6}$alkyl-sulfinyl-C$_{1-6}$alkyl, C$_{1-6}$alkyl-sulfonyl-C$_{1-6}$alkyl, amino-C$_{1-6}$alkyl, N—C$_{1-6}$alkylamino-C$_{1-6}$ alkyl, and N,N-di-C$_{1-6}$alkylamino-C$_{1-6}$alkyl.

In certain embodiments of formula I, R$^3$ is C$_{1-6}$alkyl selected from methyl, ethyl, propyl, isopropyl, n-butyl, isobutyl, tert-butyl, n-pentyl and isopentyl.

In certain embodiments of formula I, R$^3$ is C$_{1-6}$alkyloxy-C$_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxybutyl, and 4-methoxy-4-methyl-pentyl.

In certain embodiments of formula I, R$^3$ is C$_{1-6}$alkylsulfanyl-C$_{1-6}$alkyl selected from methylsulfanylmethyl, ethylsulfanylmethyl, 2-(methylsulfanyl)-ethyl, 2-(ethylsulfanyl)-ethyl, 3-(methylsulfanyl)-propyl, 3-(ethylsulfanyl)-propyl, 3-methanesulfanyl-3-methyl-butyl, 4-methanesulfanyl-butyl, and 4-methylsulfanyl-4-methyl-pentyl.

In certain embodiments of formula I, R$^3$ is C$_{1-6}$alksulfonyl-C$_{1-6}$alkyl selected from methanesulfonylmethyl, ethylsulfonylmethyl, 2-(methanesulfonyl)-ethyl, 2-(ethylsulfonyl)-ethyl, 3-(methanesulfonyl)-propyl, 3-(ethylsulfonyl)-propyl, 3-methanesulfonyl-3-methyl-butyl, 4-methanesulfonyl-butyl, 4-methanesulfonyl-4-methyl-pentyl and 2-methanesulfonyl-1-methyl-ethyl.

In certain embodiments of formula I, R$^3$ is hydroxy-C$_{1-6}$alkyl selected from 1-(2-hydroxyethyl)-3-hydroxypropyl, 1-hydroxymethyl-2-hydroxypropyl, 1-hydroxymethyl-3-hydroxypropyl, 2-hydroxy-1-methylethyl, 2-hydroxypropyl, 1,1-dimethyl-2-hydroxyethyl, 1-(hydroxymethyl)propyl, 2-hydroxyethyl, or 3-hydroxypropyl, 2-hydroxypropyl.

In certain embodiments of formula I, R$^3$ is amino-C$_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

In certain embodiments of formula I, R$^3$ is N—C$_{1-6}$alkyl-amino-C$_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

In certain embodiments of formula I, R$^3$ is N,N-di-C$_{1-6}$alkyl-amino-C$_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl.

In certain embodiments of formula I, $R^4$ is:

$C_{1-6}$alkyl selected from methyl, ethyl, propyl, isopropyl, n-butyl, isobutyl, tert-butyl, n-pentyl and isopentyl;

$C_{3-6}$cycloalkyl selected from cyclopropyl, cyclobutyl, cyclopentyl and cyclohexyl, each optionally substituted;

$C_{3-6}$cycloalkyl-$C_{1-6}$alkyl selected from cyclopropyl-$C_{1-6}$alkyl, cyclobutyl-$C_{1-6}$alkyl, cyclopentyl-$C_{1-6}$alkyl and cyclohexyl-$C_{1-6}$alkyl, the cycloalkyl portion of each being optionally substituted; or hetero-$C_{1-6}$alkyl selected from $C_{1-6}$alkyloxy-$C_{1-6}$alkyl, hydroxy-$C_{1-6}$alkyl, $C_{1-6}$alkylsulfanyl-$C_{1-6}$alkyl, $C_{1-6}$alkylsulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl.

heterocyclyl selected from piperidinyl, tetrahydropyranyl, pyrrolidinyl, tetrahydrofuranyl and tetrahydrothiopyranyl, each optionally substituted.

In certain embodiments of formula I, $R^4$ is $C_{1-6}$alkyl selected from methyl, ethyl, propyl, isopropyl, n-butyl, isobutyl, tert-butyl, n-pentyl and isopentyl.

In certain embodiments of formula I, $R^4$ is $C_{1-6}$alkyloxy-$C_{1-6}$alkyl selected from methoxymethyl, ethoxymethyl, 2-(methoxy)-ethyl, 2-(ethoxy)-ethyl, 3-(methoxy)-propyl, 3-(ethoxy)-propyl, 3-methoxy-3-methyl-butyl, 4-methoxybutyl, and 4-methoxy-4-methyl-pentyl.

In certain embodiments of formula I, $R^4$ is: $C_{1-6}$alkylsulfanyl-$C_{1-6}$alkyl selected from methylsulfanylmethyl, ethylsulfanylmethyl, 2-(methylsulfanyl)-ethyl, 2-(ethylsulfanyl)-ethyl, 3-(methylsulfanyl)-propyl, 3-(ethylsulfanyl)-propyl, 3-methanesulfanyl-3-methyl-butyl, 4-methanesulfanyl-butyl, and 4-methylsulfanyl-4-methyl-pentyl.

In certain embodiments of formula I, $R^4$ is $C_{1-6}$alksulfonyl-$C_{1-6}$alkyl selected from methanesulfonylmethyl, ethylsulfonylmethyl, 2-(methanesulfonyl)-ethyl, 2-(ethylsulfonyl)-ethyl, 3-(methanesulfonyl)-propyl, 3-(ethylsulfonyl)-propyl, 3-methanesulfonyl-3-methyl-butyl, 4-methanesulfonyl-butyl, 4-methanesulfonyl-4-methyl-pentyl and 2-methanesulfonyl-1-methyl-ethyl.

In certain embodiments of formula I, $R^4$ is hydroxy-$C_{1-6}$alkyl selected from 1-(2-hydroxyethyl)-3-hydroxypropyl, 1-hydroxymethyl-2-hydroxypropyl, 1-hydroxymethyl-3-hydroxypropyl, 2-hydroxy-1-methylethyl, 2-hydroxypropyl, 1,1-dimethyl-2-hydroxyethyl, 1-(hydroxymethyl)propyl, 2-hydroxyethyl, or 3-hydroxypropyl, 2-hydroxypropyl.

In certain embodiments of formula I, $R^4$ is amino-$C_{1-6}$alkyl selected from amino-methyl, 2-amino-ethyl, 3-amino-propyl, 2-amino-propyl, 2-amino-2-methyl-propyl, 3-amino-3-methylbutyl, 4-amino-4-methylpentyl, 2-amino-2-ethyl-propyl, 3-amino-3-ethylbutyl and 4-amino-4-ethylpentyl.

In certain embodiments of formula I, $R^4$ is N—$C_{1-6}$alkyl-amino-$C_{1-6}$alkyl selected from N-methylaminomethyl, 2-(N-methylamino)-ethyl, 3-(N-methylamino)-propyl, 2-(N-methylamino)-propyl, 2-(N-methylamino)-2-methyl-propyl, 3-(N-methylamino)-3-methylbutyl, 4-(N-methylamino)-4-methylpentyl, 2-(N-methylamino)-2-ethyl-propyl, 3-(-methylamino)-3-ethylbutyl 4-(N-methylamino)-4-ethylpentyl, N-ethylaminomethyl, 2-(N-ethylamino)-ethyl, 3-(N-ethylamino)-propyl, 2-(N-ethylamino)-propyl, 2-(N-ethylamino)-2-methyl-propyl, 3-(N-ethylamino)-3-methylbutyl, 4-(N-ethylamino)-4-methylpentyl, 2-(N-ethylamino)-2-ethyl-propyl, 3-(N-ethylamino)-3-ethylbutyl, and 4-(N-ethylamino)-4-ethylpentyl.

In certain embodiments of formula I, $R^4$ is N,N-di-$C_{1-6}$alkyl-amino-$C_{1-6}$alkyl selected from N,N-dimethylaminomethyl, 2-(N,N-dimethylamino)-ethyl, 3-(N,N-dimethylamino)-propyl, 2-(N,N-dimethylamino)-propyl, 2-(N,N-dimethylamino)-2-methyl-propyl, 3-(N,N-dimethylamino)-3-methylbutyl, 4-(N,N-dimethylamino)-4-methylpentyl, 2-(N,N-dimethylamino)-2-ethyl-propyl, 3-(N,N-dimethylamino)-3-ethylbutyl 4-(N,N-dimethylamino)-4-ethylpentyl, N,N-diethylaminomethyl, 2-(N,N-diethylamino)-ethyl, 3-(N,N-diethylamino)-propyl, 2-(N,N-diethylamino)-propyl, 2-(N,N-diethylamino)-2-methyl-propyl, 3-(N,N-diethylamino)-3-methylbutyl, 4-(N,N-diethylamino)-4-methylpentyl, 2-(N,N-diethylamino)-2-ethyl-propyl, 3-(N,N-diethylamino)-3-ethylbutyl, and 4-(N,N-diethylamino)-4-ethylpentyl.

In certain embodiments of formula I, $R^4$ is heterocyclyl selected from piperidinyl, tetrahydropyranyl, pyrrolidinyl, tetrahydrofuranyl and tetrahydrothiopyranyl, each optionally substituted.

In certain embodiments of formula I, $R^4$ is piperidinyl optionally substituted at the 4-position with $C_{1-6}$alkyl-, $C_{1-6}$alkyl-sulfonyl or acetyl, or tetrahydropyranyl.

In certain embodiments of formula I, $R^4$ is tetrahydropyranyl.

In certain embodiments of formula I, $R^4$ is hydroxy-$C_{1-6}$alkyl.

In certain embodiments of formula I, $R^4$ is $C_{1-6}$alkylsulfonyl-$C_{1-6}$alkyl.

In certain embodiments of formula I, $R^2$ is optionally substituted oxadiazoylyl.

In certain embodiments of formula I, $R^4$ is tetrahydropyranyl and $R^2$ is optionally substituted oxadiazoylyl.

In certain embodiments of formula I, $R^4$ is tetrahydropyranyl, $R^2$ is optionally substituted oxadiazoylyl and R' is methyl.

In certain embodiments of formula I, $R^4$ is tetrahydropyranyl, $R^2$ is optionally substituted oxadiazoylyl, $R^1$ is methyl and $R^3$ is methyl.

In certain embodiments of formula I, $R^4$ is tetrahydropyranyl and $R^2$ is —C(O)—NR$^b$R$^c$.

In certain embodiments of formula I, $R^4$ is tetrahydropyranyl and $R^2$ is —C(O)—NR$^d$—NR$^e$—R$^f$.

In certain embodiments of formula I:

$R^1$ is methyl;

$R^2$ is:
 an optionally substituted five membered monocyclic heteroaryl selected from oxazolyl, isoxazolyl, imidazolyl, oxadiazolyl, and triazolyl, each optionally substituted;
 —C(O)—NHR$^c$;
 —C(O)—OR$^a$;
 —C(O)—NH—NH—R$^f$;

$R^3$ is:
 methyl;
 cyclopropyl; or
 cyclopentyl; and $R^4$ is:
 hydroxy-$C_{1-6}$alkyl;
 $C_{1-6}$alkyl-sulfonyl-$C_{1-6}$alkyl; or
 tetrahydropyran-4-yl.

In certain embodiments of formula I:

$R^1$ is methyl;

$R^2$ is:
 an optionally substituted five membered monocyclic heteroaryl selected from isoxazolyl, imidazolyl, oxadiazolyl and triazolyl; or
 —C(O)—NHR$^c$ wherein R$^c$ is hydrogen, $C_{1-6}$alkyl, cyclopropyl or $C_{1-6}$alkoxy;

—C(O)—NR$^d$—NR$^e$—R$^f$ wherein R$^f$ is hydrogen, C$_{1-6}$alkyl, halo-C$_{1-6}$alkyl, or aryl-C$_{1-6}$alkylcarbonyl;

R$^3$ is methyl; and

R$^4$ is:
hydroxy-C$_{1-6}$alkyl;
C$_{1-6}$alkyl-sulfonyl-C$_{1-6}$alkyl; or
tetrahydropyran-4-yl.

In certain embodiments of formula I,

R$^1$ is methyl;

R$^2$ is an optionally substituted five membered monocyclic heteroaryl selected from isoxazolyl, imidazolyl, oxadiazolyl and triazolyl;

R$^3$ is methyl; and

R$^4$ is tetrahydropyran-4-yl.

In certain embodiments of formula I, R$^2$ is isoxazolyl, imidazolyl, oxadiazolyl or triazolyl, each optionally substituted with: C$_{1-6}$alkyl; halo-C$_{1-6}$alkyl; C$_{1-6}$alkoxy; halo-C$_{1-6}$alkoxy; hetero-C$_{1-6}$alkyl; cyano; nitro, amino; N—C$_{1-6}$alkylamino; N,N-di-(C$_{1-6}$alkyl)-amino; C$_{1-6}$alkylsulfonyl-C$_{1-6}$alkyl; C$_{3-6}$cycloalkyl; C$_{3-6}$cycloalkyl-C$_{1-6}$alkyl; aryl; aryl-C$_{1-6}$alkyl; heteroaryl; or heteroaryl-C$_{1-6}$alkyl; or —(CH$_2$)$_m$—X—(CH$_2$)$_n$—C(O)—(CH$_2$)$_p$—Y—(CH$_2$)$_q$—R$^g$, wherein m, n, p, q each independently is 0 or 1, X and Y each independently is —O—, —NR$^h$— or a bond, R$^g$ is hydrogen, C$_{1-6}$alkyl, C$_{1-6}$alkoxy, amino, N—C$_{1-6}$alkylamino or N,N-di-(C$_{1-6}$alkyl)-amino, and R$^h$ is hydrogen or C$_{1-6}$alkyl.

In certain embodiments of formula I, R$^2$ is oxadiazolyl optionally substituted with C$_{1-6}$alkyl, halo-C$_{1-6}$alkyl; or aryl-C$_{1-6}$alkyl.

In certain embodiments of the invention the subject compounds may be represented by formula II:

wherein R$^2$ and R$^3$ are as defined herein.

In certain embodiments of formula II, R$^3$ is C$_{1-6}$alkyl, C$_{3-6}$cycloalkyl or hetero-C$_{1-6}$alkyl.

In certain embodiments of formula II, R$^2$ is —C(O)—NR$^a$R$^b$, —C(O)—NR$^d$—NR$^e$—R$^f$ or an optionally substituted five membered monocyclic heteroaryl.

In certain embodiments of formula II, R$^2$ is oxazolyl, thiazolyl, isoxazolyl, isothiazolyl, imidazolyl, pyrazolyl, oxadiazolyl, thiadiazolyl or triazolyl, each optionally substituted.

In certain embodiments of formula II, R$^2$ is —C(O)—NR$^c$R$^c$.

In certain embodiments of formula II, R$^2$ is —C(O)—NHR$^c$ and R$^c$ is C$_{1-6}$alkyl, C$_{1-6}$alkoxy or C$_{3-6}$cycloalkyl.

In certain embodiments of formula II, R$^2$ is —C(O)—NR$^d$—NR$^e$—R$^f$ and R$^f$ is hydrogen, C$_{1-6}$alkyl, halo-C$_{1-6}$alkyl, or aryl-C$_{1-6}$alkylcarbonyl.

In certain embodiments of formula II, R$^2$ is —C(O)—NH—NH—R$^f$ and R$^f$ is hydrogen, halo-C$_{1-6}$alkyl or aryl-C$_{1-6}$alkyl-carbonyl.

In certain embodiments of formula II, R$^2$ is —C(O)—OR$^a$.

In certain embodiments of formula II, R$^2$ is isoxazolyl, imidazolyl, oxadiazolyl or triazolyl, each optionally substituted.

In certain embodiments of formula II, R$^3$ is:
C$_{1-6}$alkyl selected from methyl, ethyl, propyl, isopropyl, n-butyl, isobutyl, tert-butyl, n-pentyl and isopentyl;
C$_{3-6}$cycloalkyl selected from cyclopropyl, cyclobutyl, cyclopentyl and cyclohexyl, each optionally substituted;
C$_{3-6}$cycloalkyl-C$_{1-6}$alkyl selected from cyclopropyl-C$_{1-6}$alkyl, cyclobutyl-C$_{1-6}$alkyl, cyclopentyl-C$_{1-6}$alkyl and cyclohexyl-C$_{1-6}$alkyl, the cycloalkyl portion of each being optionally substituted; or
hetero-C$_{1-6}$alkyl selected from C$_{1-6}$alkyloxy-C$_{1-6}$alkyl, hydroxy-C$_{1-6}$alkyl, C$_{1-6}$alkylsulfanyl-C$_{1-6}$alkyl, C$_{1-6}$alkylsulfinyl-C$_{1-6}$alkyl, C$_{1-6}$alkyl-sulfonyl-C$_{1-6}$alkyl, amino-C$_{1-6}$alkyl, N—C$_{1-6}$alkylamino-C$_{1-6}$alkyl, and N,N-di-C$_{1-6}$alkylamino-C$_{1-6}$alkyl.

In certain embodiments of formula II, R$^2$ is optionally substituted oxadiazoylyl.

In certain embodiments of formula II:

R$^2$ is:
cyano;
an optionally substituted five membered monocyclic heteroaryl selected from oxazolyl, isoxazolyl, imidazolyl, oxadiazolyl, and triazolyl, each optionally substituted;
—C(O)—NHR$^c$;
—C(O)—OR$^a$;
—C(O)—NH—NH—R$^f$; and R$^3$ is:
methyl;
cyclopropyl; or
cyclopentyl.

In certain embodiments of formula II:

R$^2$ is:
an optionally substituted five membered monocyclic heteroaryl selected from isoxazolyl, imidazolyl, oxadiazolyl and triazolyl; or
—C(O)—NHR$^c$ wherein R$^c$ is hydrogen, C$_{1-6}$alkyl, cyclopropyl or C$_{1-6}$alkoxy;
—C(O)—NR$^d$—NR$^e$—R$^f$ wherein R$^f$ is hydrogen, C$_{1-6}$alkyl, halo-C$_{1-6}$alkyl, or aryl-C$_{1-6}$alkylcarbonyl; and R$^3$ is methyl.

In certain embodiments of formula II, R$^2$ is an optionally substituted five membered monocyclic heteroaryl selected from isoxazolyl, imidazolyl, oxadiazolyl and triazolyl, and R$^3$ is methyl.

In certain embodiments of formula II, R$^2$ is isoxazolyl, imidazolyl, oxadiazolyl or triazolyl, each optionally substituted with: C$_{1-6}$alkyl; halo-C$_{1-6}$alkyl; C$_{1-6}$alkoxy; halo-C$_{1-6}$alkoxy; hetero-C$_{1-6}$alkyl; cyano; nitro, amino; N—C$_{1-6}$alkylamino; N,N-di-(C$_{1-6}$alkyl)-amino; C$_{1-6}$alkylsulfonyl-C$_{1-6}$alkyl; C$_{3-6}$cycloalkyl; C$_{3-6}$cycloalkyl-C$_{1-6}$alkyl; aryl; aryl-C$_{1-6}$alkyl; heteroaryl; or heteroaryl-C$_{1-6}$alkyl; or —(CH$_2$)$_m$—X—(CH$_2$)$_n$—C(O)—(CH$_2$)$_p$—Y—(CH$_2$)$_q$—R$^g$, wherein m, n, p, q each independently is 0 or 1, X and Y each independently is —O—, —NR$^h$— or a bond, R$^g$ is hydrogen, C$_{1-6}$alkyl, C$_{1-6}$alkoxy, amino, N—C$_{1-6}$alkylamino or N,N-di-(C$_{1-6}$alkyl)-amino, and R$^h$ is hydrogen or C$_{1-6}$alkyl.

In certain embodiments of formula I, R$^2$ is oxadiazolyl optionally substituted with C$_{1-6}$alkyl, halo-C$_{1-6}$alkyl; or aryl-C$_{1-6}$alkyl.

In certain embodiments of the invention the subject compounds may be represented by formula III:

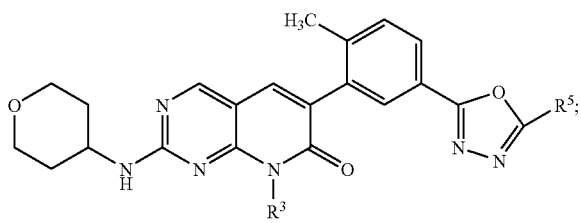

wherein R⁵ is:
hydrogen;
$C_{1-6}$alkyl;
halo-$C_{1-6}$alkyl;
$C_{1-6}$alkoxy;
halo-$C_{1-6}$alkoxy;
hetero-$C_{1-6}$alkyl;
cyano;
nitro;
amino;
N—$C_{1-6}$alkylamino;
N,N-di-($C_{1-6}$alkyl)-amino;
$C_{1-6}$alkylsulfonyl-$C_{1-6}$alkyl;
$C_{3-6}$cycloalkyl;
$C_{3-6}$cycloalkyl-$C_{1-6}$alkyl;
aryl;
aryl-$C_{1-6}$alkyl;
heteroaryl;
heteroaryl-$C_{1-6}$alkyl; or
—$(CH_2)_m$—X—$(CH_2)_n$—C(O)—$(CH_2)_p$—Y—$(CH_2)_q$—$R^g$
wherein
m, n, p, q each independently is 0 or 1;
X and Y each independently is a bond, —O—, or —NR wherein $R^h$ is hydrogen or $C_{1-6}$alkyl; and
$R^g$ is hydrogen, $C_{1-6}$alkyl, $C_{1-6}$alkoxy, amino, N—$C_{1-6}$alkylamino or
N,N-di-($C_{1-6}$alkyl)-amino; and
$R^2$ and $R^3$ are as defined herein.

In certain embodiments of formula III, $R^3$ is $C_{1-6}$alkyl, $C_{3-6}$cycloalkyl or hetero-$C_{1-6}$alkyl.

In certain embodiments of formula III, $R^3$ is methyl, cyclopropyl or cyclopentyl.

In certain embodiments of formula III, $R^5$ is hydrogen, $C_{1-6}$alkyl, halo-$C_{1-6}$alkyl, $C_{1-6}$alkoxy, halo-$C_{1-6}$alkoxy, hetero-$C_{1-6}$alkyl, cyano, nitro, amino, N—$C_{1-6}$alkylamino N,N-di-($C_{1-6}$alkyl)-amino, aryl-$C_{1-6}$alkyl, or heteroaryl-$C_{1-6}$alkyl.

In certain embodiments of formula III, $R^5$ is hydrogen, $C_{1-6}$alkyl, halo-$C_{1-6}$alkyl, $C_{1-6}$alkoxy, halo-$C_{1-6}$alkoxy, or benzyl, the phenyl portion of which may be optionally substituted.

In certain embodiments of formula III, $R^5$ is hydrogen, $C_{1-6}$alkyl, halo-$C_{1-6}$alkyl, benzyl, 3-chlorobenzyl or 4-chlorobenzyl.

In certain embodiments of formula III, $R^3$ is $C_{1-6}$alkyl, $C_{3-6}$cycloalkyl or hetero-$C_{1-6}$alkyl, and $R^5$ is hydrogen, $C_{1-6}$alkyl, halo-$C_{1-6}$alkyl, benzyl, 3-chlorobenzyl or 4-chlorobenzyl.

In embodiments of the invention where any of $R^1$, $R^2$, $R^3$, $R^4$, $R^5$, $R^a$, $R^b$, $R^c$, $R^d$, $R^e$, $R^f$, $R^g$ and $R^h$ is alkyl or contains an alkyl moiety, such alkyl is preferably lower alkyl, i.e. $C_1$-$C_6$alkyl, and more preferably $C_1$-$C_4$alkyl.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with one aspect of the invention are shown below in Table 1.

TABLE 1

| # | Structure | Name (Autonom™) | MP/M + H |
|---|---|---|---|
| 1 | 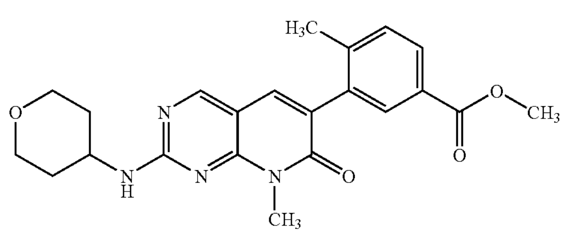 | 4-Methyl-3-[8-methyl-7-oxo-2-(tetrahydro-pyran-4-ylamino)-7,8-dihydro-pyrido[2,3-d]pyrimidin-6-yl]-benzoic acid methyl ester | 122.5-126.5° C. |

TABLE 1-continued

| # | Structure | Name (Autonom ™) | MP/M + H |
|---|---|---|---|
| 2 | 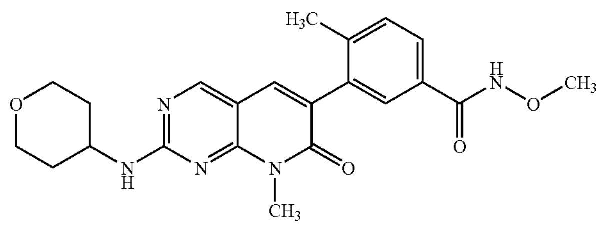 | N-Methoxy-4-methyl-3-[8-methyl-7-oxo-2-(tetrahydro-pyran-4-ylamino)-7,8-dihydro-pyrido[2,3-d]pyrimidin-6-yl]-benzamide | 206.5-210.6° C. |
| 3 | 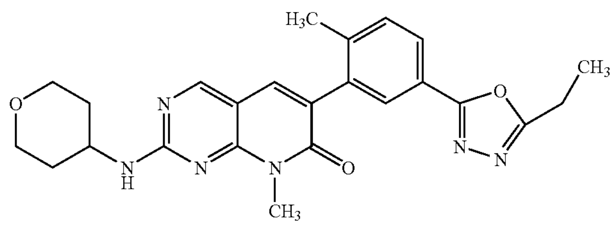 | 6-[5-(5-Ethyl-[1,3,4]oxadiazol-2-yl)-2-methyl-phenyl]-8-methyl-2-(tetrahydro-pyran-4-ylamino)-8H-pyrido[2,3-d]pyrimidin-7-one | 224.9-226.0° C. |
| 4 | 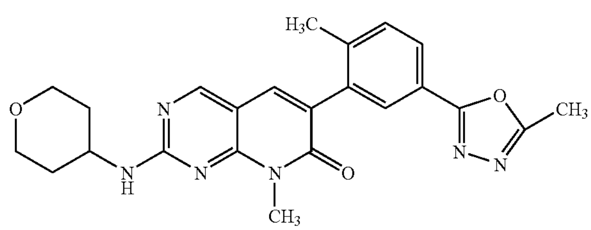 | 8-Methyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one | 235.0-238.4° C. |
| 5 | 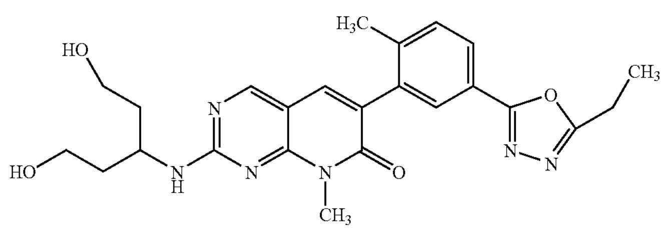 | 6-[5-(5-Ethyl-[1,3,4]oxadiazol-2-yl)-2-methyl-phenyl]-2-[3-hydroxy-1-(2-hydroxy-ethyl)-propylamino]-8-methyl-8H-pyrido[2,3-d]pyrimidin-7-one | 113.5-115.2° C. |
| 6 | 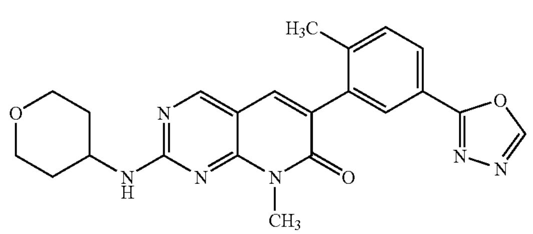 | 8-Methyl-6-(2-methyl-5-[1,3,4]oxadiazol-2-yl-phenyl)-2-(tetrahydro-pyran-4-ylamino)-8H-pyrido[2,3 | 197.0-200.0° C. |
| 7 | 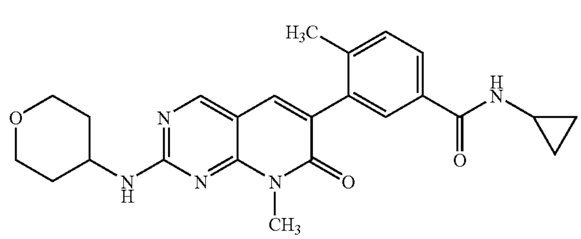 | N-Cyclopropyl-4-methyl-3-[8-methyl-7-oxo-2-(tetrahydro-pyran-4-ylamino)-7,8-dihydro-pyrido[2,3-d]pyrimidin-6-yl]-benzamide | 239.3-241.0° C. |

TABLE 1-continued

| # | Structure | Name (Autonom ™) | MP/M + H |
|---|---|---|---|
| 8 | 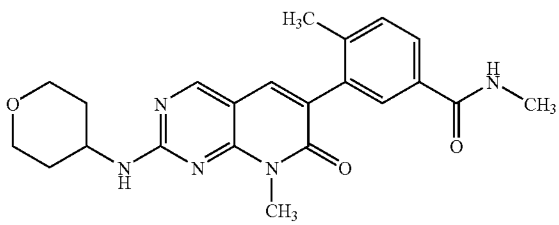 | 4,N-Dimethyl-3-[8-methyl-7-oxo-2-(tetrahydro-pyran-4-ylamino)-7,8-dihydro-pyrido[2,3-d]pyrimidin-6-yl]-benzamide | 206.5-210.6° C. |
| 9 | 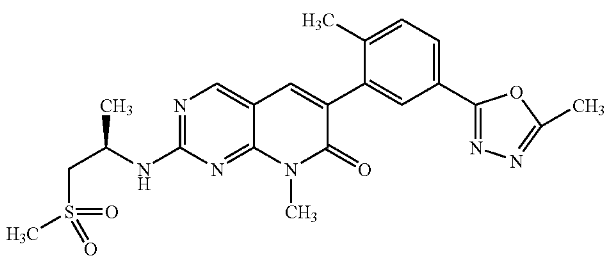 | 2-(2-Methanesulfonyl-1-methyl-ethylamino)-8-methyl-6-[2-methyl-5-(5-methyl-[1,3,4]oxadiazol-2-yl)-phenyl]-8H-pyrido[2,3-d]pyrimidin-7-one | 469 |
| 10 | 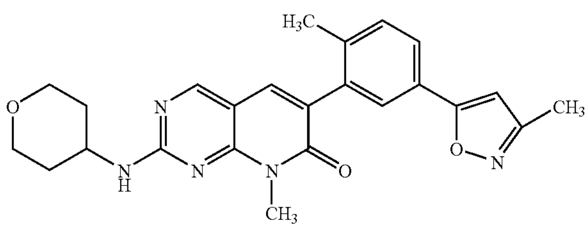 | 8-Methyl-6-[2-methyl-5-(3-methyl-isoxazol-5-yl)-phenyl]-2-(tetrahydro-pyran-4-ylamino)-8H-pyrido[2,3-d]pyrimidin-7-one | 432 |
| 11 | 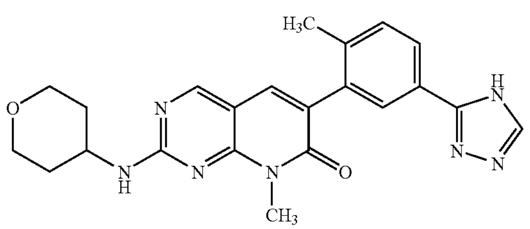 | 8-Methyl-6-[2-methyl-5-(4H-[1,2,4]triazol-3-yl)-phenyl]-2-(tetrahydro-pyran-4-ylamino)-8H-pyrido[2,3-d]pyrimidin-7-one | 214.9-216.0° C. |
| 12 | 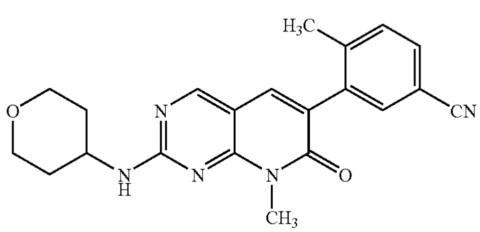 | 4-Methyl-3-[8-methyl-7-oxo-2-(tetrahydro-pyran-4-ylamino)-7,8-dihydro-pyrido[2,3-d]pyrimidin-6-yl]-benzonitrile | 253.5-254.1° C. |
| 13 | 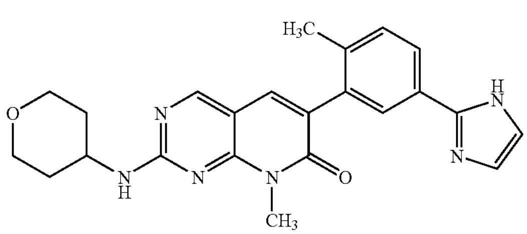 | 6-[5-(1H-Imidazol-2-yl)-2-methyl-phenyl]-8-methyl-2-(tetrahydro-pyran-4-ylamino)-8H-pyrido[2,3-d]pyrimidin-7-one | 417 |

TABLE 1-continued

| # | Structure | Name (Autonom ™) | MP/M + H |
|---|---|---|---|
| 14 | 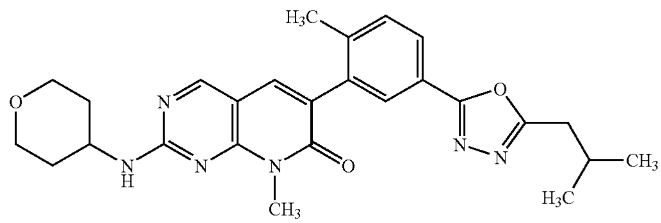 | 6-[5-(5-Isobutyl-[1,3,4]oxadiazol-2-yl)-2-methyl-phenyl]-8-methyl-2-(tetrahydro-pyran-4-ylamino)-8H-pyrido[2,3-d]pyrimidin-7-one | 475 |
| 15 | 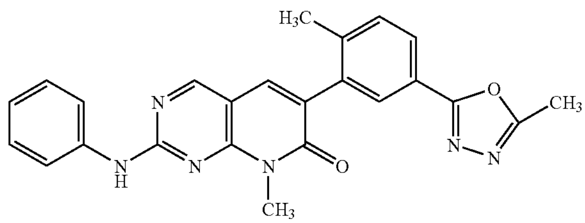 | 8-Methyl-6-[2-methyl-5-(5-methyl-[1,3,4]oxadiazol-2-yl)-phenyl]-2-phenylamino-8H-pyrido[2,3-d]pyrimidin-7-one | 275.0-278.8° C. |
| 16 | 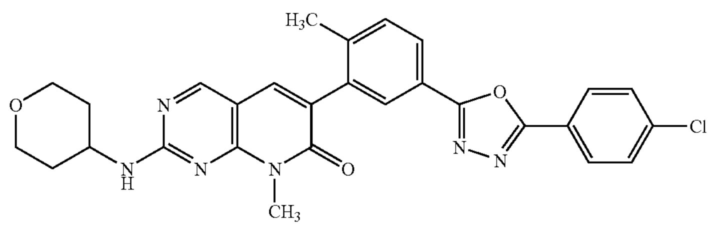 | 6-{5-[5-(4-Chloro-phenyl)-[1,3,4]oxadiazol-2-yl]-2-methyl-phenyl}-8-methyl-2-(tetrahydro-pyran-4-ylamino)-8H-pyrido[2,3-d]pyrimidin-7-one | 529 |
| 17 | 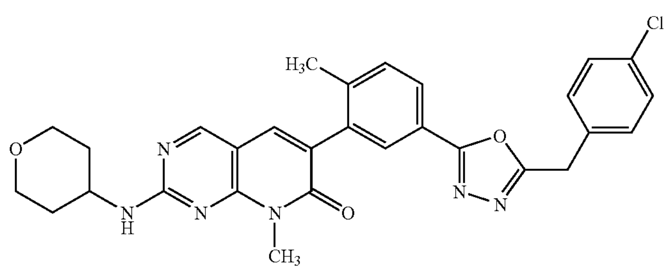 | 6-{5-[5-(4-Chloro-benzyl)-[1,3,4]oxadiazol-2-yl]-2-methyl-phenyl}-8-methyl-2-(tetrahydro-pyran-4-ylamino)-8H-pyrido[2,3-d]pyrimidin-7-one | 543 |
| 18 | 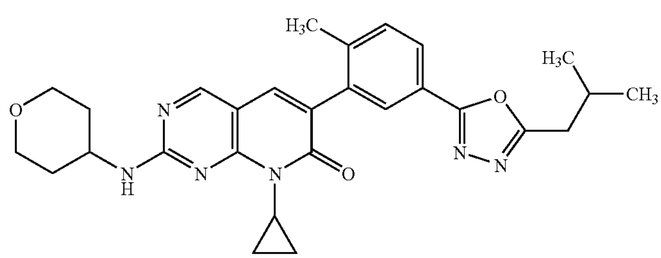 | 8-Cyclopropyl-6-[5-(5-isobutyl-[1,3,4]oxadiazol-2-yl)-2-methyl-phenyl]-2-(tetrahydro-pyran-4-ylamino)-8H-pyrido[2,3-d]pyrimidin-7-one | 501 |
| 19 | 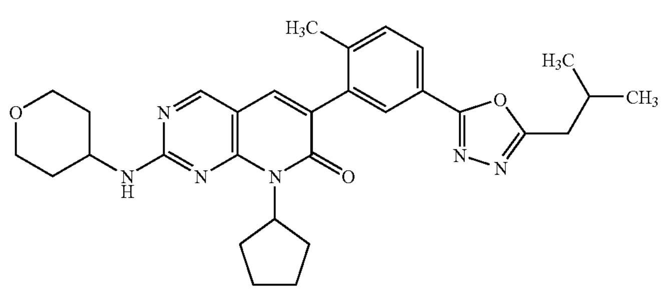 | 8-Cyclopentyl-6-[5-(5-isobutyl-[1,3,4]oxadiazol-2-yl)-2-methyl-phenyl]-2-(tetrahydro-pyran-4-ylamino)-8H-pyrido[2,3-d]pyrimidin-7-one | 529 |

TABLE 1-continued

| # | Structure | Name (Autonom ™) | MP/M + H |
|---|---|---|---|
| 20 | 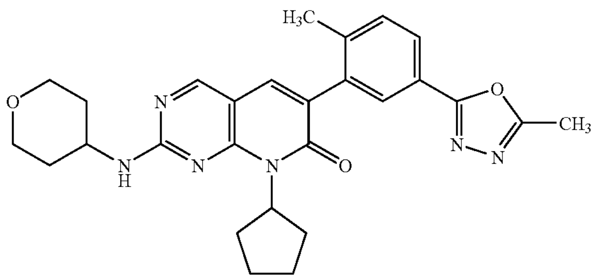 | 8-Cyclopentyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one | 487 |
| 21 | 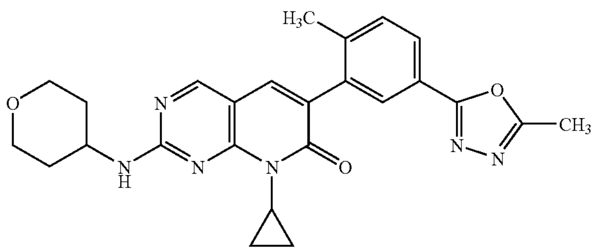 | 8-Cyclopropyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one | 459 |
| 22 | 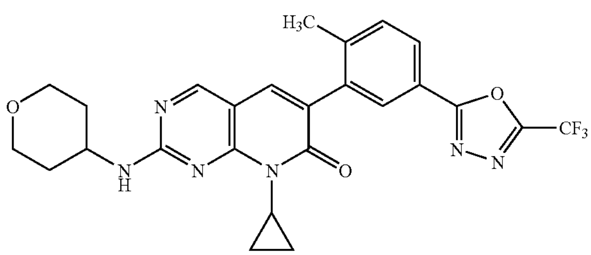 | 8-Cyclopropyl-6-[2-methyl-5-(5-trifluoromethyl-[1,3,4]oxadiazol-2-yl)-phenyl]-2-(tetrahydro-pyran-4-ylamino)-8H-pyrido[2,3-d]pyrimidin-7-one | 513 |
| 23 | 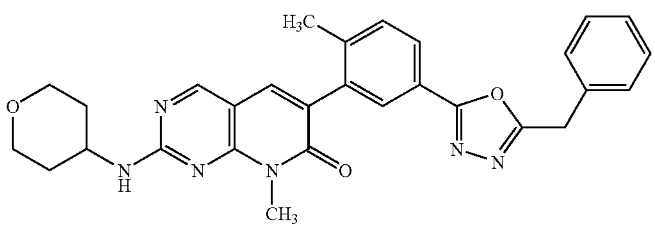 | 6-[5-(5-Benzyl-[1,3,4]oxadiazol-2-yl)-2-methyl-phenyl]-8-methyl-2-(tetrahydro-pyran-4-ylamino)-8H-pyrido[2,3-d]pyrimidin-7-one | 509 |
| 24 | 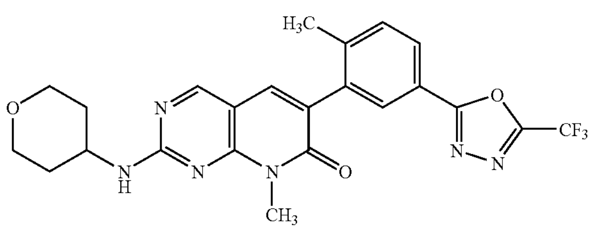 | 8-Methyl-6-[2-methyl-5-(5-trifluoromethyl-[1,3,4]oxadiazol-2-yl)-phenyl]-2-(tetrahydro-pyran-4-ylamino)-8H-pyrido[2,3-d]pyrimidin-7-one | 487 |
| 25 | 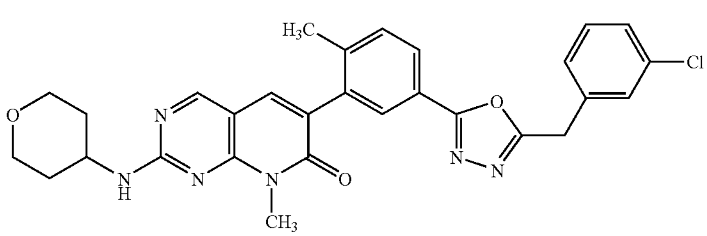 | 6-{5-[5-(3-Chloro-benzyl)-[1,3,4]oxadiazol-2-yl]-2-methyl-phenyl}8-methyl-2-(tetrahydro-pyran-4-ylamino)-8H-pyrido[2,3-d]pyrimidin-7-one | 543 |

TABLE 1-continued

| # | Structure | Name (Autonom ™) | MP/M + H |
|---|---|---|---|
| 26 | 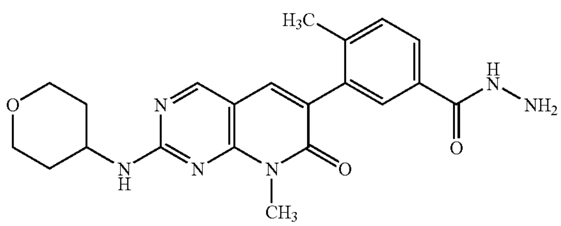 | 4-Methyl-3-[8-methyl-7-oxo-2-(tetrahydro-pyran-4-ylamino)-7,8-dihydro-pyrido[2,3-d]pyrimidin-6-yl]-benzoic acid hydrazide | 409 |
| 27 | 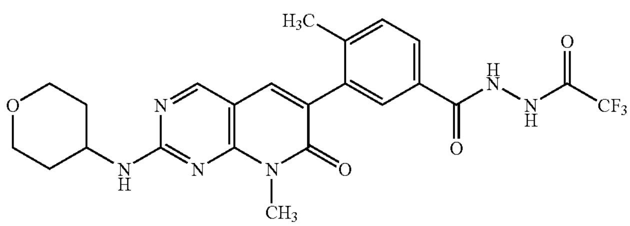 | 4-Methyl-3-[8-methyl-7-oxo-2-(tetrahydro-pyran-4-ylamino)-7,8-dihydro-pyrido[2,3-d]pyrimidin-6-yl]-benzoic acid N'-(2,2,2-trifluoro-acetyl)-hydrazide | 505 |
| 28 | 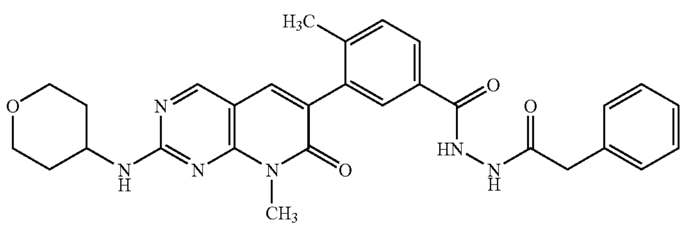 | 4-Methyl-3-[8-methyl-7-oxo-2-(tetrahydro-pyran-4-ylamino)-7,8-dihydro-pyrido[2,3-d]pyrimidin-6-yl]-benzoic acid N'-phenylacetyl-hydrazide | 527 |
| 29 | 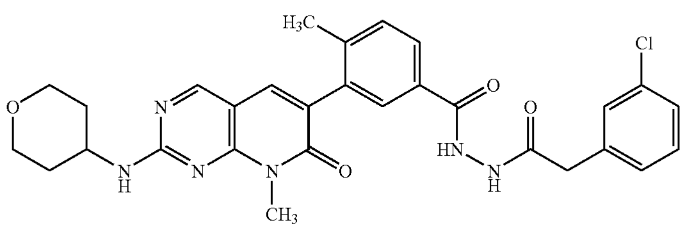 | 4-Methyl-3-[8-methyl-7-oxo-2-(tetrahydro-pyran-4-ylamino)-7,8-dihydro-pyrido[2,3-d]pyrimidin-6-yl]-benzoic acid N'-[2-(3-chloro-phenyl)-acetyl]-hydrazide | 561 |

Synthesis

Compounds of the present invention can be made by a variety of methods depicted in the illustrative synthetic reaction schemes shown and described below.

The starting materials and reagents used in preparing these compounds generally are available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One specific method for preparing pyrimido-pyridone compounds of the invention is shown in Scheme A below, wherein "Het" is heteroaryl, R is lower alkyl, and $R^4$, $R^5$ and $R^a$ are as defined herein.

SCHEME A

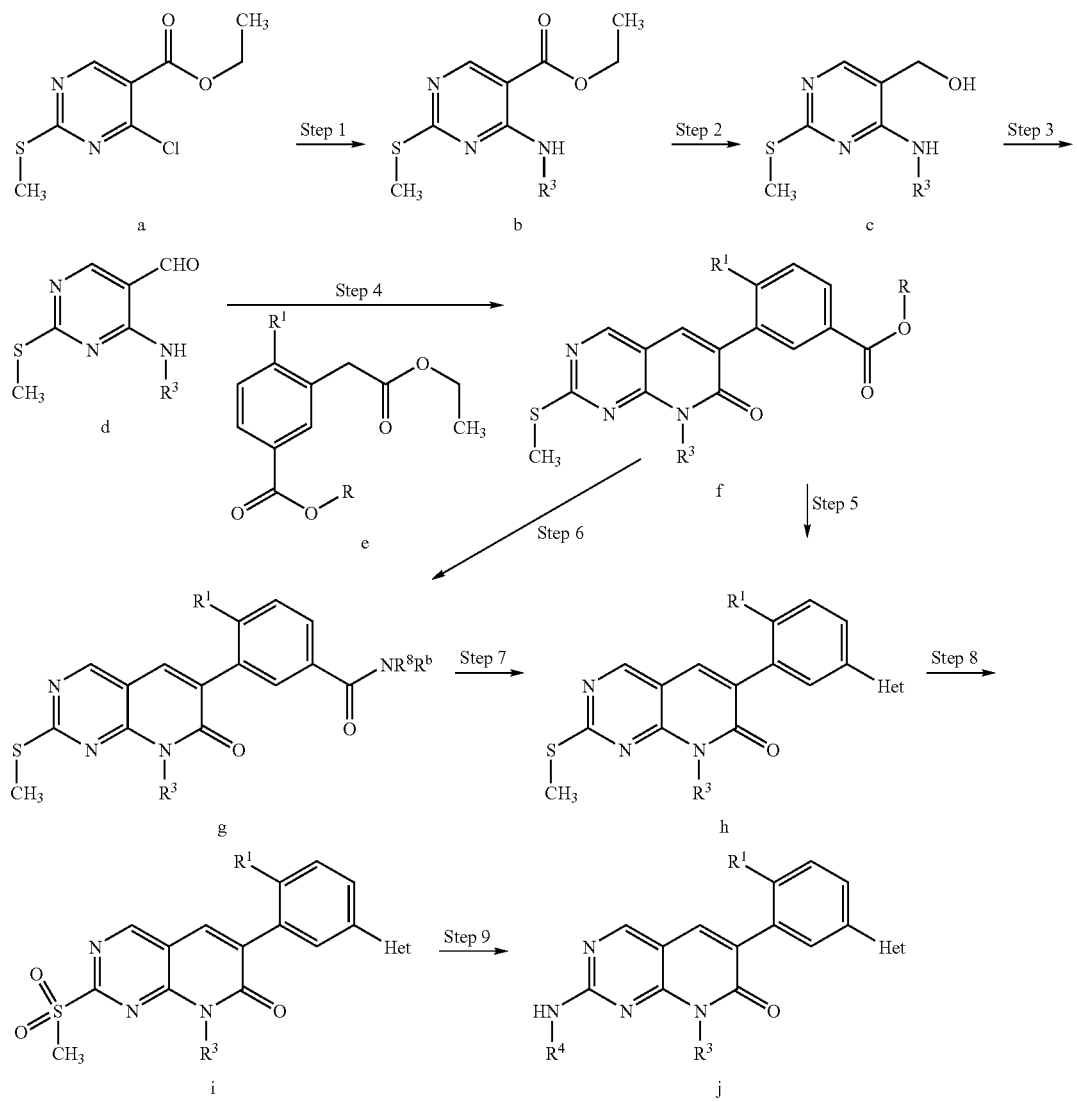

In step 1 of Scheme A, treatment of pyrimidine a with a primary amine $R^3$—$NH_2$ under polar aprotic solvent conditions provides compound b. Reduction of the ester group on compound b in step 2 provides an alcohol c. Oxidation of alcohol compound c in step 3 provides carboxaldehyde compound d. In step 4, reaction of carboxaldehyde d with diester compound e in the presence of a base provides a pyrimidopyridone compound f.

In step 5, the ester group of compound f may undergo suitable reaction to form a heteroaryl-substituted compound h. For example, treatment of compound f with propan-2-one oxime under basic conditions, followed by acid, will provide an isoxazole. Alternatively, the ester group of compound f may be reduced to an alcohol and then selectively oxidized to an aldehyde group, and the aldehyde compound may be treated with glyoxal and ammonium hydroxide to yield an imidazolyl group.

Step 6 may be carried out instead of step 5, by reaction of compound f with amine $HNR^aR^b$ to afford amide compound g. Amide compound g may then undergo suitable reaction to form a heteroaryl-substituted compound h. For example, where $R^a$ and $R^b$ are hydrogen, treatment of compound g with dimethylformamide dimethylacetal followed by hydrazine affords a triazinyl group.

The sulfanyl group of compound h may then be oxidized in step 8 by treatment with peracid to afford sulfone compound i. In step 9, the sulfone group of compound i is displaced by reaction with amine $R^4$—$NH_2$ to afford compound j, which is a compound of formula I in accordance with the invention.

Many variations of the procedure of Scheme A are possible and will suggest themselves to those skilled in the art. For example, in step 6 compound f may be treated with a hydrazine instead of an amine to afford a hydrazide compound (not shown) which could then be converted into an oxadiazole, thiadiazole, triazole, or other heteroaryl group in a subsequent reaction. The sulfanyl groups of compounds f and g may be oxidized as described in step 8, and subject to reaction with an amine as described in step 9, with subsequent steps 5, 7, 8 and 9 omitted, to yield additional compounds of the invention.

Referring now to Scheme B, another procedure for making compounds of the invention is shown wherein R is lower alkyl, and wherein $R^1$, $R^3$, $R^4$ and $R^5$ are as defined herein.

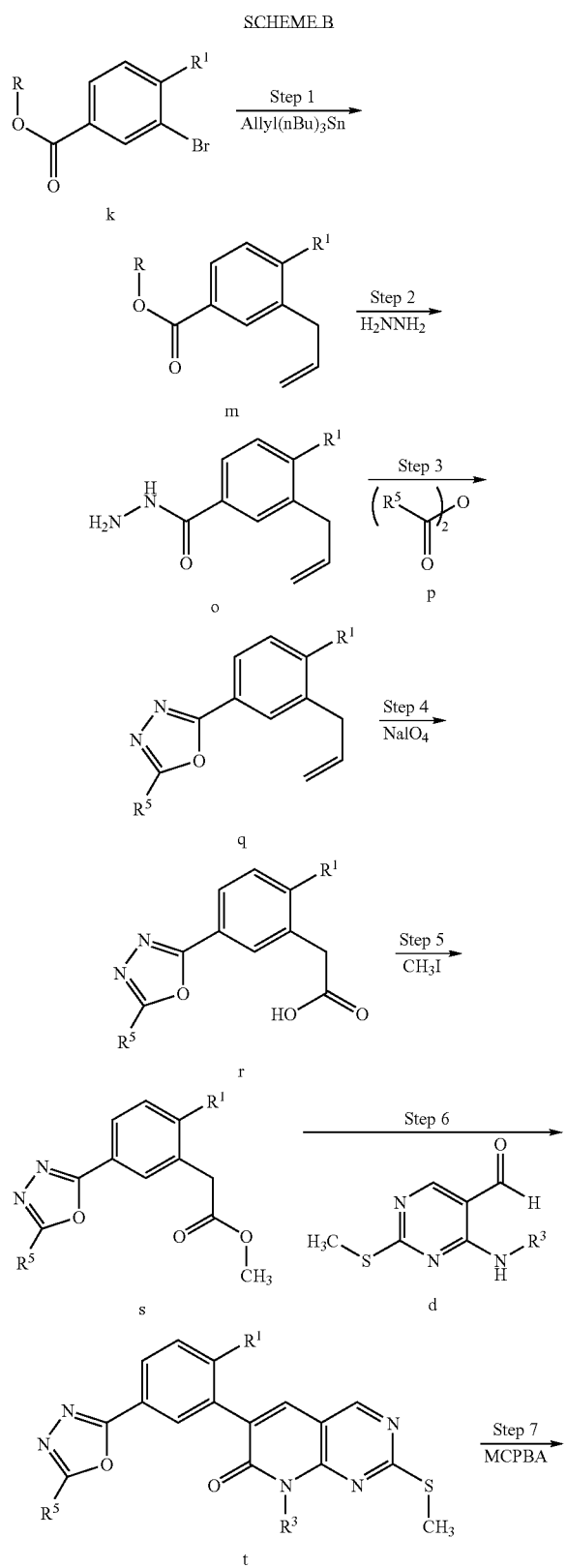

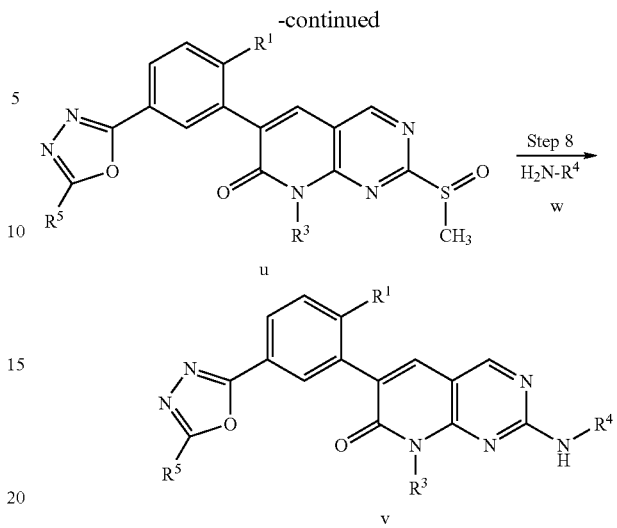

In step 1 of Scheme B, bromobenzoic acid ester k is allylated by treatment with an alkylating agent such as an allyl trialkyl stannane, to afford allyl benzoic acid ester compound m. Compound m is then reacted with hydrazine in step 2 to give hydrazide compound o. The hydrazide compound o is then subjected to reaction with anhydride p in step 3 to yield phenyl oxadiazole compound q. In step 4, the allyl group of compound q is oxidized with periodate or other oxidizing reagent to afford phenylacetic acid compound r. In step 5, a phenylacetic acid methyl ester compound s is formed by treatment of compound r with methyl iodide. Compound s is then reacted with sulfanyl pyrimidine carboxaldehyde d in step 6 to provide sulfanyl pyrimido-pyridone compound t. In step 7 the sulfanyl group of compound t is subject to oxidation by treatment with peracid or like oxidizing reagent to afford sulfinyl pyrimido-pyridone compound u. Compound u is then reacted with amine w in step 8 to afford compound v, which is a compound of formula I in accordance with the invention.

As in the case of Scheme A, many variation on the procedure of Scheme B are possible. In one such variation, a substituted hydrazine may be reacted in step 2 with compound m, and steps 3-5 may then be omitted to afford hydrazide compounds of formula I. The oxidation of step 7 may in some embodiments provide a sulfonyl compound instead of a sulfinyl compound as shown in Scheme B. Other variation of Scheme B will be readily apparent to those skilled in the art.

Specific details of Scheme A and B are provided in the Examples below.

Pharmaceutical Compositions And Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

Compounds of the invention are also useful for the treatment of disorders or disease states in humans or other mammals, which are exacerbated or caused by Raf, or otherwise associated with modulation of Raf. Accordingly, the invention provides methods for treating Raf mediated proliferative disorders such as melanoma, multiple myeloma, thyroid cancer, colon cancer, restenosis, angiogenesis, diabetic retinopathy, psoriasis, surgical adhesions, macular degeneration, and atherosclerosis.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; opthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), cancer, multiple myeloma, and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

| ABBREVIATIONS | |
|---|---|
| DCM | dichloromethane/methylene chloride |
| DMF | N,N-dimethylformamide |
| DMAP | 4-dimethylaminopyridine |
| DMFDMA | dimethylformamide dimethylacetal |
| ECDI | 1-ethyl-3-(3'-dimethylaminopropyl)carbodiimide |
| EtOAc | ethyl acetate |
| EtOH | ethanol |
| gc | gas chromatography |
| HMPA | hexamethylphosphoramide |
| HOAc | acetic acid |
| HOBt | N-Hydroxybenzotriazole |
| hplc | high performance liquid chromatography |
| LDA | lithium diisopropylamine |
| LAH | litium aluminum hydride |
| mCPBA | m-chloroperbenzoic acid |
| MeCN | acetonitrile |
| MeOH | methanol |
| NMP | N-methyl pyrrolidinone |
| TEA | triethylamine |
| THF | tetrahydrofuran |
| TLC | thin layer chromatography |
| OXONE ™ | potassium peroxy-monosulfate |

Preparation 1

3-Ethoxycarbonylmethyl-4-methyl-benzoic acid methyl ester

The synthetic procedure of Preparation 1 is shown in Scheme C.

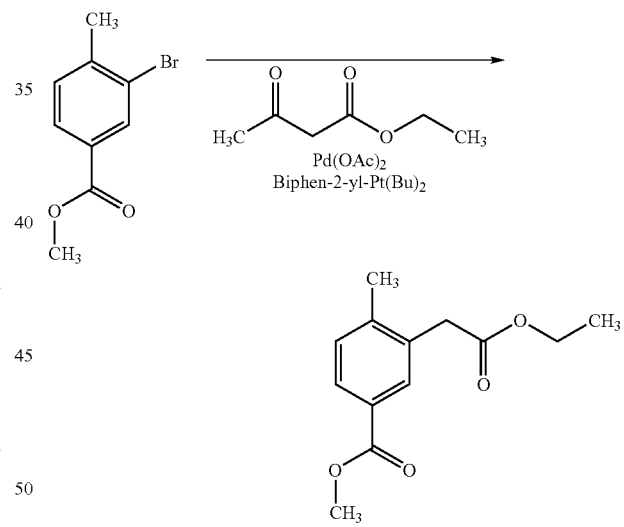

3-Bromo-4-methyl-benzoic acid methyl ester (20.0 g, 87.31 mmol) was dissolved in 220 mL toluene, and 3-oxobutyric acid ethyl ester (25.0 g, 192.08 mmol), $K_3PO_4$ (102 g, 480 mmol), biphen-2-yl-P(t-Bu)$_2$ (2.60 g, 8.73 mmol), and palladium diacetate (980 mg, 4.36 mmol) were added. The reaction mixture was evacuated and purged with argon, and then heated to 90° C. for 15 hours. The reaction mixture was cooled and partitioned between water and ethyl acetate. The organic layer was washed with water, brine, dried (MgSO$_4$), filtered, and concentrated under reduced pressure. The residue was purified by flash chromatography (10%-15% EtOAc/hexanes) to provide 2.20 g of 3-ethoxycarbonylmethyl-4-methyl-benzoic acid methyl ester, MS (M+H)=237.

Preparation 2

4-Methylamino-2-methylthiopyrimidine-5-carboxaldehyde

The synthetic procedure of this preparation is shown in Scheme D.

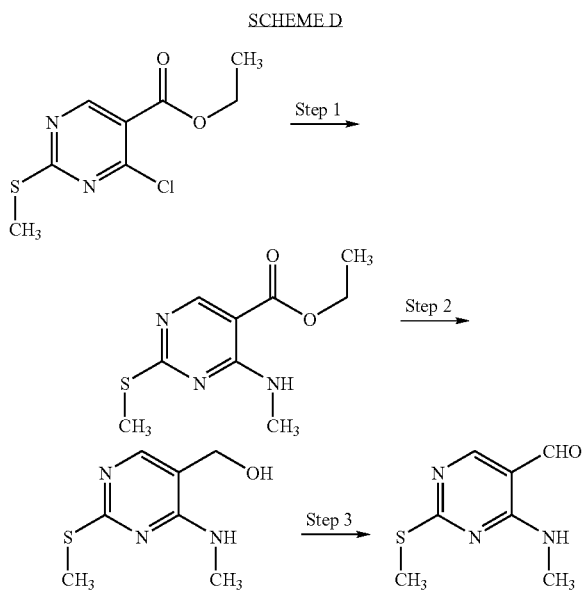

SCHEME D

Step 1 4-Methylamino-2-methylsulfanyl-pyrimidine-5-carboxylic acid ethyl ester Following generally the procedure of VanderWel, S. N. et al. *J. Med. Chem.* 2005, 48, 2371-2387), to a solution of ethyl 4-chloro-2-methylthiopyrimidine-5-carboxylate (Aldrich, 20 g, 86 mmol) in 250 mL of dichloromethane at 0° C. was added slowly a solution of methylamine in ethanol (33%, 35 mL 281 mmol). After stirring for 30 minutes, water (150 mL) was added and the phases were separated. The organic phase was dried ($MgSO_4$) and filtered. The filtrate was evaporated under reduced pressure to give 19 g of 4-methylamino-2-methylsulfanyl-pyrimidine-5-carboxylic acid ethyl ester as a white solid. MS (M+H)=228.

Step 2 (4-Methylamino-2-methylsulfanyl-pyrimidin-5-yl)-methanol

Lithium aluminum hydride (8.2 g, 215 mmol) was stirred in dry tetrahydrofuran (300 mL) at 5° C. and treated dropwise with a solution of ethyl 4-methylamino-2-methylthio-pyrimidine-5-carboxylate (46 g, 215 mmol) in dry tetrahydrofuran (450 mL). The reaction mixture was stirred for 15 minutes and then water (18 mL) was added dropwise with caution. The reaction was stirred for 30 minutes and then an aqueous solution of sodium hydroxide (15%, 8.5 mL) was added dropwise, followed by water (25.5 mL). The resulting suspension was stirred for 17 hours at room temperature and then filtered. The filter residue was washed with tetrahydrofuran and the combined filtrate and washings were evaporated under reduced pressure. The residue was suspended in ethyl acetate/hexanes—½ (200 mL) and the solid was filtered and dried to provide 32.7 g of (4-methylamino-2-methylsulfanyl-pyrimidin-5-yl)-methanol as a yellow solid. MS (M+H)=186.

Step 3 4-Methylamino-2-methylthiopyrimidine-5-carboxaldehyde (4-Methylamino-2-methylsulfanyl-pyrimidin-5-yl)-methanol (20 g, 108 mmol) and 1 L of dichloromethane were combined with stirring and treated with manganese dioxide (87 g, 1 mol). The resulting suspension was stirred for 24 hours and then filtered through Celite. The filter residue was washed with dichloromethane (100 mL) and the combined filtrate and washings were evaporated under reduced pressure to give 15.8 g of 4-methylamino-2-methylthiopyrimidine-5-carboxaldehyde as a white solid. MS (M+H)=184.

Similarly prepared were:
4-Cyclopentylamino-2-methylsulfanyl-pyrimidine-5-carbaldehyde, MS (M+H)=238; and
4-cyclopropylamino-2-methyl-sulfanyl-pyrimidine-5-carbaldehyde, MS (M+H)=210.

Preparation 3

4-Methyl-3-(8-methyl-2-methylsulfanyl-7-oxo-7,8-dihydro-pyrido[2,3-d]pyrimidin-6-yl)-benzoic acid methyl ester The synthetic procedure of this Preparation is shown in Scheme E.

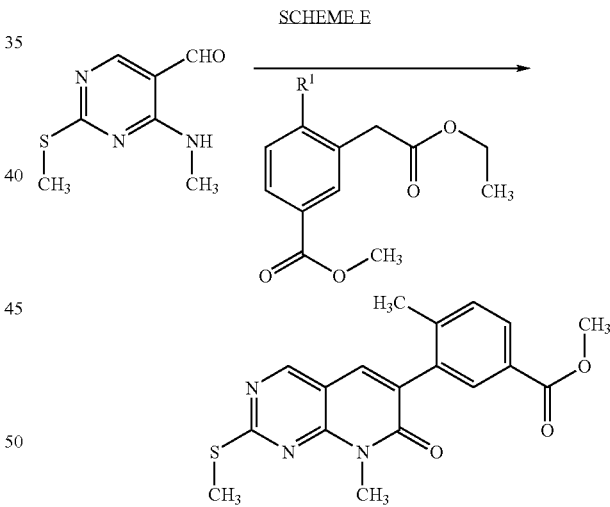

SCHEME E

3-Ethoxycarbonylmethyl-4-methyl-benzoic acid methyl ester (2.18 g, 9.22 mmol), 4-methylamino-2-methylthiopyrimidine-5-carboxaldehyde (1.69 g, 9.22 mmol) and $K_2CO_3$ (2.55 g, 18.44 mmol) were added to 23 mL NMP, and the reaction mixture was heated to 90° C. with stirring for 9 hours, then cooled and stirred at room temperature for 10 hours. The reaction mixture was diluted with 100 mL water, and the resulting precipitate was collected by filtration, washed with water, and dried to give 3.09 g of 4-methyl-3-(8-methyl-2-methylsulfanyl-7-oxo-7,8-dihydro-pyrido[2,3-d]pyrimidin-6-yl)-benzoic acid methyl ester: MS (M+H)=356.

Example 1

N-Cyclopropyl-4-methyl-3-[8-methyl-7-oxo-2-(tetrahydro-pyran-4-ylamino)-7,8-dihydro-pyrido[2,3-d]pyrimidin-6-yl]-benzamide The synthetic procedure of this Example is shown in Scheme F.

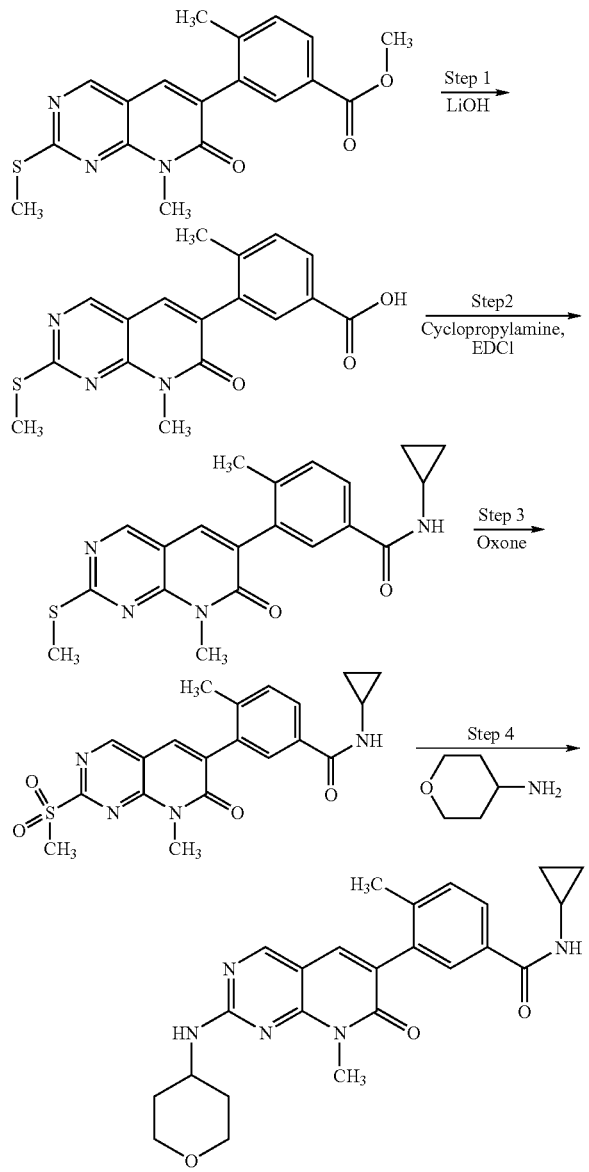

Step 1 4-Methyl-3-(8-methyl-2-methylsulfanyl-7-oxo-7,8-dihydro-pyrido[2,3-d]pyrimidin-6-yl)-benzoic acid 4-Methyl-3-(8-methyl-2-methylsulfanyl-7-oxo-7,8-dihydro-pyrido[2,3-d]pyrimidin-6-yl)-benzoic acid methyl ester (1.0 g, 2.81 mmol) was dissolved in 4 mL THF, and 1.0 M aqueous LiOH (2.8 mL, 2.81 mmol) was added. The reaction mixture was stirred at room temperature for 100 hours, then was partitioned between diethyl ether and water. The aqueous layer was acidified by addition of 5% aqueous HCl, and the resulting precipitate was collected by filtration, washed with water, and dried under vacuum to provide 820 mg of 4-methyl-3-(8-methyl-2-methylsulfanyl-7-oxo-7,8-dihydro-pyrido[2,3-d]pyrimidin-6-yl)-benzoic acid MS (M+H)=342.

Step 2 N-Cyclopropyl-4-methyl-3-(8-methyl-2-methylsulfanyl-7-oxo-7,8-dihydro-pyrido[2,3-d]pyrimidin-6-yl)-benzamide 4-Methyl-3-(8-methyl-2-methylsulfanyl-7-oxo-7,8-dihydro-pyrido[2,3-d]pyrimidin-6-yl)-benzoic acid (150 mg, 0.44 mmol) was taken up in 2 mL DMF, and cyclopropylamine (50 mg, 0.88 mmol) was added, followed by EDCI (1.2 g, 0.527 mmol, 1.2 eq.). The reaction mixture was stirred at room temperature for 90 minutes, then partitioned between water and EtOAc. The organic layer was washed with brine, dried over MgSO$_4$, filtered and concentrated under reduced pressure. The residue was purified by preparative thin layer chromatography (EtOAc/hexanes 1:1) to give 25 mg of N-cyclopropyl-4-methyl-3-(8-methyl-2-methylsulfanyl-7-oxo-7,8-dihydro-pyrido[2,3-d]pyrimidin-6-yl)-benzamide MS (M+H)=381.

Step 3 N-Cyclopropyl-3-(2-methanesulfonyl-8-methyl-7-oxo-7,8-dihydro-pyrido[2-d]pyrimidin-6-yl)-4-methyl-benzamide N-Cyclopropyl-4-methyl-3-(8-methyl-2-methylsulfanyl-7-oxo-7,8-dihydro-pyrido[2,3-d]pyrimidin-6-yl)-benzamide (21 mg) was dissolved in a mixture of 2 mL MeOH, 1 mL THF and 1 mL water. OXONE™ (1.63 mg, 0.09 mmol) was added, and the reaction mixture was stirred for three hours at room temperature. The reaction mixture was then partitioned between water and EtOAc, and the organic layer was washed with brine, dried over MgSO$_4$, filtered and concentrated under reduced pressure to give 25 mg of N-cyclopropyl-3-(2-methanesulfonyl-8-methyl-7-oxo-7,8-dihydro-pyrido[2,3-d]pyrimidin-6-yl)-4-methyl-benzamide.

Step 4 N-Cyclopropyl-4-methyl-3-[8-methyl-7-oxo-2-(tetrahydro-pyran-4-ylamino)-7,8-dihydro-pyrido[2,3-d]pyrimidin-6-yl]-benzamide 4-Amino-tetrahydropyran (11 mg, 0.106 mmol) was dissolved in 2 mL THF, and N-cyclopropyl-3-(2-methanesulfonyl-8-methyl-7-oxo-7,8-dihydro-pyrido[2,3-d]pyrimidin-6-yl)-4-methyl-benzamide (21 mg, 0.051 mmol) was added. The reaction mixture was stirred for 6.5 hours at room temperature, and then 1 mL MeOH was added. The resulting mixture was loaded directly onto a preparative TLC plate and eluted with 5% MeOH in methylene chloride to give N-cyclopropyl-4-methyl-3-[8-methyl-7-oxo-2-(tetrahydro-pyran-4-ylamino)-7,8-dihydro-pyrido[2,3-d]pyrimidin-6-yl]-benzamide: MS (M+H)=434; MP=239.3-241.0° C.

Similarly prepared, replacing cyclopropylamine with methylamine, was 4,N-Ddimethyl-3-[8-methyl-7-oxo-2-(tetrahydro-pyran-4-ylamino)-7,8-dihydro-pyrido[2,3-d]pyrimidin-6-yl]-benzamide: MS (M+H)=408; MP=268.2-270.0°C.

Example 2

4-Methyl-3-[8-methyl-7-oxo-2-(tetrahydro-pyran-4-ylamino)-7,8-dihydro-pyrido[2,3-d]pyrimidin-6-yl]-benzonitrile The synthetic procedure of this Example is shown in Scheme G.

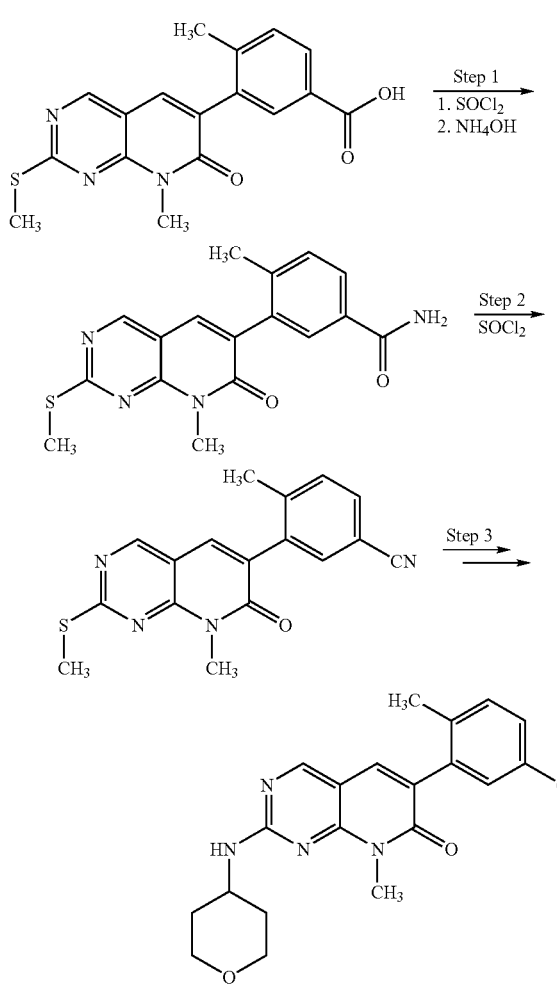

Step 1 4-Methyl-3-(8-methyl-2-methylsulfanyl-7-oxo-7,8-dihydro-pyrido[2,3-d]pyrimidin-6-yl)-benzamide 4-Methyl-3-(8-methyl-2-methylsulfanyl-7-oxo-7,8-dihydro-pyrido[2,3-d]pyrimidin-6-yl)-benzoic acid (384 mg) was stirred in 10 g of $SOCl_2$ for one hour. The reaction mixture was concentrated under reduced pressure. To the residue was added 10 mL of EtOAc and 5 mL of saturated aqueous $NH_4OH$. The reaction mixture was stirred for 20 minutes, and then 10 mL THF was added. The reaction mixture was partitioned between water and methylene chloride, and the organic layer was dried over $MgSO_4$, filtered, and concentrated under reduced pressure to give 372 mg of 4-methyl-3-(8-methyl-2-methylsulfanyl-7-oxo-7,8-dihydro-pyrido[2,3-d]pyrimidin-6-yl)-benzamide: MS (M+H)=341.

Step 2 4-Methyl-3-(8-methyl-2-methylsulfanyl-7-oxo-7,8-dihydro-pyrido[2,3-d]pyrimidin-6-yl)-benzonitrile 4-Methyl-3-(8-methyl-2-methylsulfanyl-7-oxo-7,8-dihydro-pyrido[2,3-d]pyrimidin-6-yl)-benzamide (24 mg) was stirred in 3 g of $SOCl_2$ for 100 hours at room temperature. Additional $SOCl_2$ (4.5 g) was then added, and the reaction mixture was heated to 75° C. for 30 minutes. The reaction mixture was concentrated under reduced pressure, and the residue was eluted with 5% MeOH in methylene chloride via preparative TLC plate to give 4-methyl-3-(8-methyl-2-methylsulfanyl-7-oxo-7,8-dihydro-pyrido[2,3-d]pyrimidin-6-yl)-benzonitrile: MS (M+H)=323.

Step 3

4-Methyl-3-(8-methyl-2-methylsulfanyl-7-oxo-7,8-dihydro-pyrido[2,3-d]pyrimidin-6-yl)-benzonitrile (49 mg, 0.15 mmol) was treated with OXONE™ following the procedure of step 3 of Example 1 to afford 4-methyl-3-(8-methyl-2-methylsulfonyl-7-oxo-7,8-dihydro-pyrido[2,3-d]pyrimidin-6-yl)-benzonitrile, which in turn was reacted with 4-amino-tetrahydropyran using the procedure of step 4 of Example 1, to give 4-methyl-3-[8-methyl-7-oxo-2-(tetrahydro-pyran-4-ylamino)-7,8-dihydro-pyrido[2,3-d]pyrimidin-6-yl]-benzonitrile: MS (M+H)=376; MP=253.5-254.1° C.

Example 3

4-Methyl-3-[8-methyl-7-oxo-2-(tetrahydro-pyran-4-ylamino)-7,8-dihydro-pyrido[2,3-d]pyrimidin-6-yl]-benzoic acid methyl ester

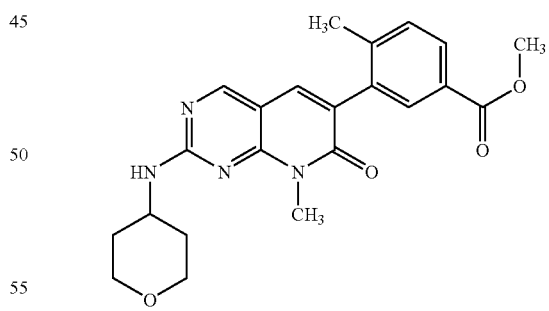

4-Methyl-3-(8-methyl-2-methylsulfanyl-7-oxo-7,8-dihydro-pyrido[2,3-d]pyrimidin-6-yl)-benzoic acid methyl ester was treated with OXONE™ following the procedure of step 3 of Example 1, and the resulting sulfonyl compound was treated with 4-amino-tetrahydropyran using the procedure of step 4 of Example 1, to give 4-methyl-3-[8-methyl-7-oxo-2-(tetrahydro-pyran-4-ylamino)-7,8-dihydro-pyrido[2,3-d]pyrimidin-6-yl]-benzoic acid methyl ester: MS (M+H)=409; MP=122.5-126.5° C.

Example 4

8-Methyl-6-[2-methyl-5-(3-methyl-isoxazol-5-yl)-phenyl]-2-(tetrahydro-pyran-4-ylamino)-8H-pyrido[2,3-d]pyrimidin-7-one The synthetic procedure of this Example is shown in Scheme H.

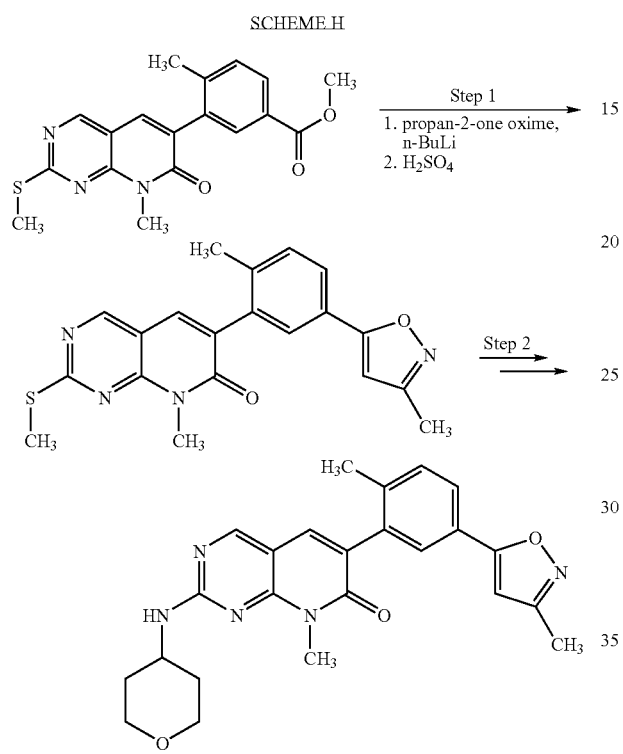

Step 1 8-Methyl-6-[2-methyl-5-(3-methyl-isoxazol-5-yl)-phenyl]-2-methylsulfanyl-8H-pyrido[2,3-d]pyrimidin-7-one Propane-2-one oxime (62 mg, 0.844 mmol) was dissolved in 2 mL THF and cooled to 0° C. under nitrogen. n-Butyl lithium (0.68 mL of 2.5 M solution in hexanes, 1.688 mmol) was added slowly, so that the reaction temperature remained below 5° C. After stirring for 30 minutes, 4-methyl-3-(8-methyl-2-methylsulfanyl-7-oxo-7,8-dihydro-pyrido[2,3-d]pyrimidin-6-yl)-benzoic acid methyl ester (200 mg, 0.56 mmol) was added, and the reaction mixture was stirred at 0° C. for one hour. Concentrated sulfuric acid (0.43 mL) was added dropwise, and the temperature was allowed to warm to room temperature over one hour. The reaction mixture was made pH neutral by addition of 1 M aqueous NaOH, and then partitioned between water and methylene chloride. The organic layer was dried over MgSO$_4$, filtered, and concentrated under reduced pressure. The residue was purified by preparative scale TLC plate, eluting with 25% EtOAc in hexanes then again with 0.25% MeOH in CH$_2$Cl$_2$, to give 8 mg of 8-methyl-6-[2-methyl-5-(3-methyl-isoxazol-5-yl)-phenyl]-2-methylsulfanyl-8H-pyrido[2,3-d]pyrimidin-7-one; MS (M+H)=379.

Step 2 8-Methyl-6-[2-methyl-5-(3-methyl-isoxazol-5-yl)-phenyl]-2-(tetrahydro-pyran-4-ylamino)-8H-pyrido[2,3-d]pyrimidin-7-one 8-Methyl-6-[2-methyl-5-(3-methyl-isoxazol-5-yl)-phenyl]-2-methylsulfanyl-8H-pyrido[2,3-d]pyrimidin-7-one was treated with OXONE™ following the procedure of step 3 of Example 1, and the resulting sulfonyl compound was treated with 4-amino-tetrahydropyran using the procedure of step 4 of Example 1, to give 8-Methyl-6-[2-methyl-5-(3-methyl-isoxazol-5-yl)-phenyl]-2-(tetrahydro-pyran-4-ylamino)-8H-pyrido[2,3-d]pyrimidin-7-one: MS (M+H)=432.

Example 5

8-Methyl-6-[2-methyl-5-[4H-1,2,4]triazol-3-yl)-phenyl]-2-(tetrahydro-pyran-4-ylamino)-8H-pyrido[2,3-d]pyrimidin-7-one The synthetic procedure of this Example is shown in Scheme I.

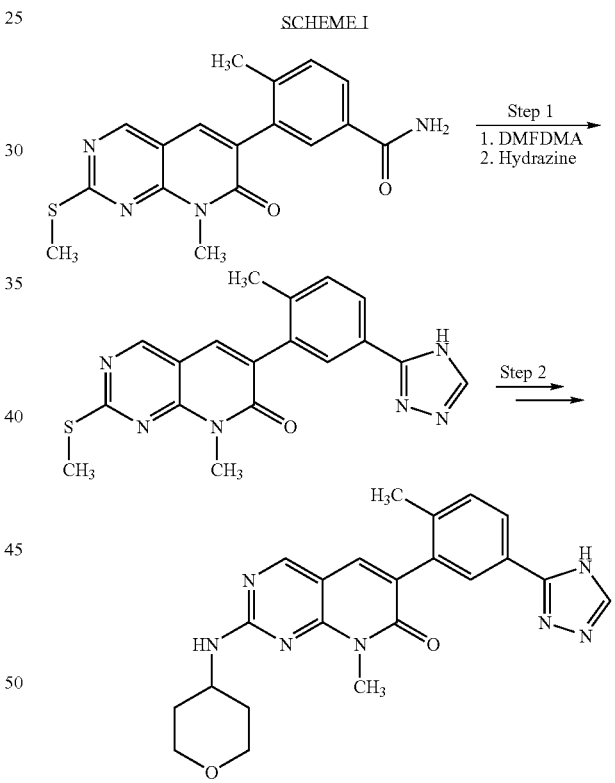

Step 1 8-Methyl-2-methylsulfanyl-6-[2-methyl-5-(4H-[1,2,4]triazol-3-yl)-phenyl]-8H-pyrido[2,3-d]pyrimidin-7-one 4-Methyl-3-(8-methyl-2-methylsulfanyl-7-oxo-7,8-dihydro-pyrido[2,3-d]pyrimidin-6-yl)-benzamide (100 mg, 0.294 mmol) was taken up in 6 mL DMFDMA, and the reaction mixture was heated to reflux for 10 minutes, then cooled and concentrated under reduced pressure. The resulting residue was taken up in 10 mL HOAc, and hydrazine (0.24 g, 7.638 mmol) was added. The reaction mixture was stirred at room temperature for 20 minutes, and the resulting precipitate was collected by filtration and washed with water to give 60 mg of 8-methyl-2-methylsulfanyl-6-[2-methyl-5-(4H-[1,2,4]triazol-3-yl)-phenyl]-8H-pyrido[2,3-d]pyrimidin-7-one, MS (M+H)=365.

Step 2 8-Methyl-6-[2-methyl-5-(4H-[1,2,4]triazol-3-yl)-phenyl]-2-(tetrahydro-pyran-4-ylamino)-8H-pyrido[2,3-d]pyrimidin-7-one 8-Methyl-2-methylsulfanyl-6-[2-methyl-5-(4H-[1,2,4]triazol-3-yl)-phenyl]-8H-pyrido[2,3-d]pyrimidin-7-one was treated with OXONE™ following the procedure of step 3 of Example 1, and the resulting sulfonyl compound was treated with 4-amino-tetrahydropyran using the procedure of step 4 of Example 1, to give 8-methyl-6-[2-methyl-5-(4H-[1,2,4]triazol-3-yl)-phenyl]-2-(tetrahydro-pyran-4-ylamino)-8H-pyrido[2,3-d]pyrimidin-7-one: MS (M+H)=418, MP=214.9-216.0° C.

Example 6

6-[5-(1H-Imidazol-2-yl)-2-methyl-phenyl]-8-methyl-2-(tetrahydro-pyran-4-ylamino)-8H-pyrido[2,3-d]pyrimidin-7-one The synthetic procedure of this Example is shown in Scheme J.

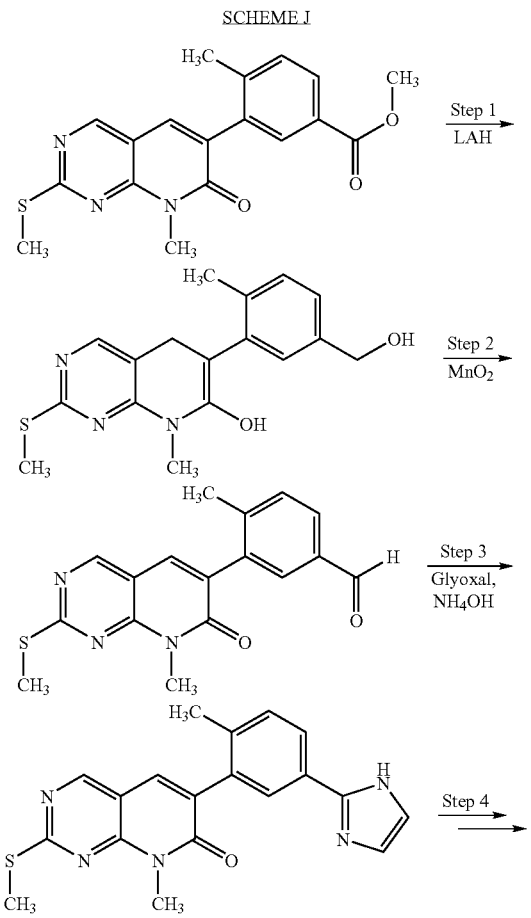

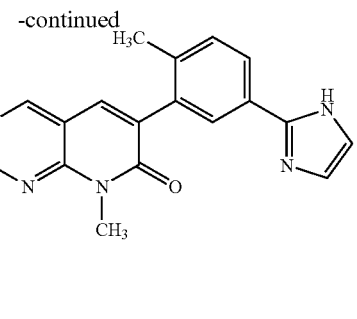

Step 1 6-(5-Hydroxymethyl-2-methyl-phenyl)-8-methyl-2-methylsulfanyl-5,8-dihydro-pyrido[2,3-d]pyrimidin-7-ol 4-Methyl-3-(8-methyl-2-methylsulfanyl-7-oxo-7,8-dihydro-pyrido[2,3-d]pyrimidin-6-yl)-benzoic acid methyl ester (150 mg, 0.422 mmol) was dissolved in 6 mL dry THF. The reaction mixture was cooled to 0° C., and LAH (0.63 mL of 1.0 M solution in THF, 0.633 mmol) was added dropwise. The reaction mixture was stirred at 0° C. for 15 minutes, and then the ice bath was removed. Water (0.3 mL) in 2 mL THF was added dropwise. After stirring for 10 minutes, 0.3 mL of 20% aqueous NaOH was added. After stirring for another 10 minutes, 0.8 mL water was added. The reaction mixture was stirred for 90 minutes, then filtered through a Celite pad. The filtrate was concentrated under reduced pressure to give 132 mg of 6-(5-Hydroxymethyl-2-methyl-phenyl)-8-methyl-2-methylsulfanyl-5,8-dihydro-pyrido[2,3-d]pyrimidin-7-ol, MS (M+H)=330.

Step 2 4-Methyl-3-(8-methyl-2-methylsulfanyl-7-oxo-7,8-dihydro-pyrido[2,3-d]pyrimidin-6-yl)-benzaldehyde 6-(5-Hydroxymethyl-2-methyl-phenyl)-8-methyl-2-methylsulfanyl-8H-pyrido[2,3-d]pyrimidin-7-one (129 mg, 0.394 mmol) was dissolved in 7 mL methylene chloride at room temperature, and MnO$_2$ (343 mg, 3.94 mmol) was added. The reaction mixture was stirred for 48 hours at room temperature, then filtered through Celite. The filtrate was concentrated under reduced pressure, and the residue was purified by preparative TLC plate, eluting with 5% MeOH/DCM, to give 73 mg of 4-methyl-3-(8-methyl-2-methylsulfanyl-7-oxo-7,8-dihydro-pyrido[2,3-d]pyrimidin-6-yl)-benzaldehyde, MS (M+H)=326.

Step 3 6-[5-(1H-Imidazol-2-yl)-2-methyl-phenyl]-8-methyl-2-methylsulfanyl-8H-pyrido[2,3-d]pyrimidin-7-one 4-Methyl-3-(8-methyl-2-methylsulfanyl-7-oxo-7,8-dihydro-pyrido[2,3-d]pyrimidin-6-yl)-benzaldehyde (69 mg, 0.212 mmol) was suspended in 3 mL EtOH, and the reaction mixture was cooled to 0° C. Glyoxal (0.049 mL of 10% aqueous solution) and 0.07 mL of saturated aqueous NH$_4$OH were added. The reaction mixture was stirred for 30 minutes at 0° C., then allowed to warm to room temperature over 60 minutes with stirring. THF (4 mL was added, and the reaction mixture was stirred for 60 minutes. Glyoxal (1.3 mL of 10% aqueous solution) was added, followed by 1.9 mL of saturated aqueous NH$_4$OH. The reaction mixture was stirred for two hours, then partitioned between water and EtOAc. The organic layer was washed with brine, dried over MgSO₄, filtered and concentrated under reduced pressure. The residue was purified by preparative TLC plate, eluting with 5% MeOH/DCM, to give 6-[5-(1H-Imidazol-2-yl)-2-methyl-phenyl]-8-methyl-2-methylsulfanyl-8H-pyrido[2,3-d]pyrimidin-7-one, MS (M+H)=464.

Step 4 6-[5-(1H-Imidazol-2-yl)-2-methyl-phenyl]-8-methyl-2-(tetrahydro-pyran-4-ylamino)-8H-pyrido[2,3-d]pyrimidin-7-one 6-[5-(1H-Imidazol-2-yl)-2-methyl-phenyl]-8-methyl-2-methylsulfanyl-8H-pyrido[2,3-d]pyrimidin-7-one was treated with OXONE™ following the procedure of step 3 of Example 1, and the resulting sulfonyl compound was treated with 4-amino-tetrahydropyran using the procedure of step 4 of Example 1, to give 2.5 mg of 6-[5-(1H-imidazol-2-yl)-2-methyl-phenyl]-8-methyl-2-(tetrahydro-pyran-4-ylamino)-8H-pyrido[2,3-d]pyrimidin-7-one: MS (M+H)=417.

Example 7

8-Cyclopentyl-6-[5-(5-isobutyl-[1,3,4]-oxadiazol-2-yl)-2-methyl-phenyl]-2-(tetrahydro-pyran-4-ylamino)-8H-pyrido[2,3-d]pyrimidin-7-one The synthetic procedure of this Example is shown in Scheme K.

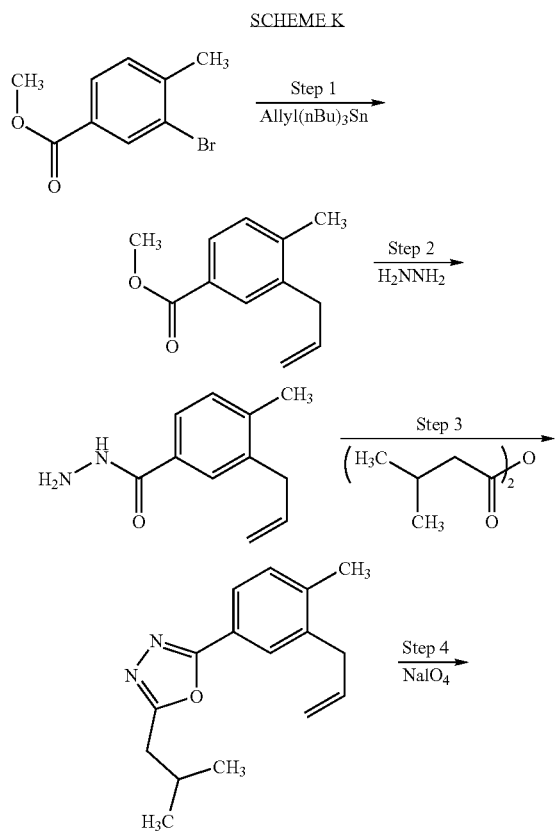

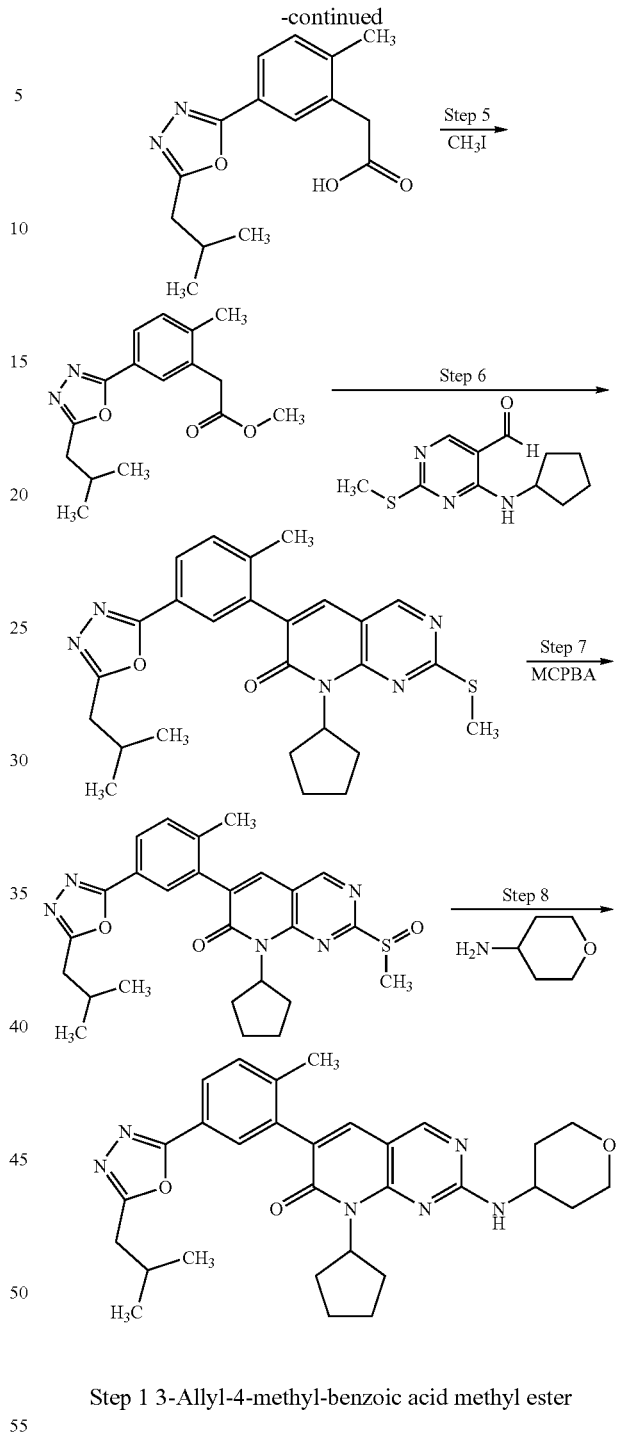

Step 1 3-Allyl-4-methyl-benzoic acid methyl ester

Argon was bubbled into a solution of methyl 3-bromo-4-methylbenzoate (11.45 g, 50 mmol), allyltributyl-stannane (16.72 g, 50.5 mmol) and lithium chloride (5.30 g, 125 mmol) in DMF (100 mL) with magnetic stirring for 20 minutes. Dichlorobis(triphenyl-phosphine)palladium (0.81 g, 1.16 mmol) was then added and mixture heated at 95° C. for 1.5 hours. After cooling to room temperature, the mixture was partitioned between ether-hexanes (1:1 V/V) and water. The combined organic layers were washed with brine, dried (MgSO₄), filtered and concentrated under reduced pressure. The residue was purified by flash chromatography (Isco RediSep 330 g silica gel, 5% then 35% dichloromethane in hexanes) to give 3-allyl-4-methyl-benzoic acid methyl ester (9.68 g, 100%) as a colorless oil.

Step 2 3-Allyl-4-methyl-benzoic acid hydrazide

A solution of methyl 3-allyl-4-methylbenzoate (2.84 g, 15 mmol) and hydrazine hydrate (2.1 mL, 37.5 mmol) in ethanol (5 mL) was heated to 100° C. for 6 hours. After cooling, the mixture was partitioned between ethyl acetate and water, and the combined organic layers were washed with brine, dried (MgSO$_4$), filtered, and concentrated under reduced pressure to give 3-allyl-4-methyl-benzoic acid hydrazide as a white solid. (Yield 2.80 g, 98.1%).

Step 3 2-(3-Allyl-4-methyl-phenyl)-5-isobutyl-[1,3,4]oxadiazole

To a solution of 3-allyl-4-methyl-benzoic acid hydrazide (1.0 g, 5.26 mmol) and diisopropylethyl-amine (6.31 mL, 36.2 mmol) in acetonitrile (30 mL) was added isovaleric anhydride (1.31 mL, 6.58 mmol), and the mixture was allowed to stir for 18 hours at room temperature. To this mixture was added triphenylphosphine (5.66 g, 21.6 mmol), followed by hexachloroethane (2.86 g, 12.11 mmol). The mixture was stirred for 5 hours at room temperature. The solvent was evaporated under reduced pressure, and the residue was purified by flash chromatography eluting with 0-30% ethyl acetate in hexanes to give 2-(3-allyl-4-methyl-phenyl)-5-isobutyl-[1,3,4]oxadiazole (Yield: 1.32 g, 98%).

Step 4 [5-(5-Isobutyl-[1,3,4]oxadiazol-2-yl)-2-methyl-phenyl]-acetic acid

To a solution of 2-(3-allyl-4-methyl-phenyl)-5-isobutyl-[1,3,4]oxadiazole (1.32 g, 5.15 mmol) in 35 mL of carbon tetrachloride and 35 mL of acetonitrile was added a solution of sodium periodate (3.26 g, 15.2 mmol) and ruthenium trichloride hydrate (0.085 g, 0.41 mmol) in water (80 mL). The mixture was stirred at room temperature for 2 hours and then was diluted with dichloromethane (200 mL). The organic layer was separated, washed with water, dried with magnesium sulfate, filtered, and evaporated under reduced pressure to give a dark oil. The oil was dissolved in tert-butyl alcohol (50 mL) and 2-methyl-2-butene (17 mL). A solution of sodium chlorite (6.52 g, 57.68 mmol) and sodium dihydrogen phosphate (5.12 g, 37.08 mmol) in water (30 mL) was added at 0° C., and the resulting mixture was stirred at 0° C. for 2 hours and then at room temperature overnight. The reaction mixture was diluted with ethyl acetate, and the organic phase was separated, washed with water, 10% sodium thiosulfate and brine, dried (magnesium sulfate), filtered and concentrated under reduced pressure. The residue was purified by flash chromatography eluting with 40-100% ethyl acetate in hexanes to give [5-(5-isobutyl-[1,3,4]oxadiazol-2-yl)-2-methyl-phenyl]-acetic acid (Yield: 1.01 g, 72%).

Step 5 [5-(5-Isobutyl-[1,3,4]oxadiazol-2-yl)-2-methyl-phenyl]-acetic acid methyl ester A suspension of potassium carbonate (0.56 g, 4.05 mmol), [5-(5-isobutyl-[1,3,4]oxadiazol-2-yl)-2-methyl-phenyl]-acetic acid (1.01 g, 3.68 mmol) and iodomethane (0.33 mL, 5.26 mmol) in N,N-dimethylformamide (10 mL) was stirred at room temperature for 2 days. The reaction mixture was partitioned between ethyl acetate and water. The combined organic phase was washed with water and brine, dried (magnesium sulfate), filtered and concentrated under reduced pressure. The residue was purified by flash chromatography eluting with 0-40% ethyl acetate in hexanes to give [5-(5-isobutyl-[1,3,4]oxadiazol-2-yl)-2-methyl-phenyl]-acetic acid methyl ester (Yield: 0.54 g, 51%).

Step 6 8-Cyclopentyl-6-{5-(5-isobutyl-[1,3,4]oxadiazol-2-yl)-2-methyl-phenyl}-2-methylsulfanyl-8H-pyrido[2,3-d]pyrimidin-7-one A mixture of 4-cyclopentylamino-2-methylsulfanyl-pyrimidine-5-carbaldehyde (0.05 g, 0.22 mmol, from Preparation 4), [5-(5-isobutyl-[1,3,4]oxadiazol-2-yl)-2-methyl-phenyl]-acetic acid methyl ester (0.06 g, 0.21 mmol) and cesium carbonate (0.14 g, 0.43 mmol) in N,N-dimethylacetamide (4 mL) was heated in a microwave reactor at 100° C. for 3.5 hours. The reaction mixture was cooled and partitioned between ethyl acetate and water. The combined organic phase was washed with water and brine, dried (magnesium sulfate), filtered and concentrated under reduced pressure. The residue was purified by flash chromatography eluting with 30% ethyl acetate in hexanes to give 8-cyclopentyl-6-{5-(5-isobutyl-[1,3,4]oxadiazol-2-yl)-2-methyl-phenyl}-2-methylsulfanyl-8H-pyrido[2,3-d]pyrimidin-7-one (Yield: 0.04 g, 40%).

Step 7 8-Cyclopentyl-6-{5-(5-isobutyl-[1,3,4]oxadiazol-2-yl)-2-methyl-phenyl}-2-methanesulfinyl-8H-pyrido[2,3-d]pyrimidin-7-one To a solution of 8-cyclopentyl-6-{5-(5-isobutyl-[1,3,4]oxadiazol-2-yl)-2-methyl-phenyl}-2-methylsulfanyl-8H-pyrido[2,3-d]pyrimidin-7-one (40.0 mg, 0.08 mmol) in dichloromethane (3 mL) at 0° C. was added 3-chloroperoxybenzoic acid (0.04 g, 0.19 mmol). The mixture was stirred at 0° C. for 1 hour, then was diluted with ethyl acetate. The organic layer was washed with saturated sodium bicarbonate solution and brine, dried (magnesium sulfate), filtered and concentrated under reduced pressure to give 8-cyclopentyl-6-{5-(5-isobutyl-[1,3,4]-oxadiazol-2-yl)-2-methyl-phenyl}-2-methanesulfinyl-8H-pyrido[2,3-d]pyrimidin-7-one (0.06 g). The crude product was used in the next step without further purification.

Step 8 8-Cyclopentyl-6-[5-(5-isobutyl-[1,3,4]oxadiazol-2-yl)-2-methyl-phenyl]-2-(tetrahydro-pyran-4-ylamino)-8H-pyrido[2,3-d]pyrimidin-7-one A mixture of 8-cyclopentyl-6-{5-(5-isobutyl-[1,3,4]oxadiazol-2-yl)-2-methyl-phenyl}-2-methane-sulfinyl-8H-pyrido[2,3-d]pyrimidin-7-one (0.04 g, 0.08 mmol) and 4-aminotetrahydropyran (0.041 g, 0.40 mmol) in 2-propanol (2 mL) was heated in a microwave reactor at 120° C. for 1 hour. The reaction mixture was cooled and concentrated under reduced pressure. The residue was purified by flash chromatography eluting with 50-70% ethyl acetate in hexanes to give 8-cyclopentyl-6-{5-(5-isobutyl-[1,3,4]oxadiazol-2-yl)-2-methyl-phenyl}-2-(tetrahydro-pyran-4-ylamino)-8H-pyrido[2,3-d]pyrimidin-7-one (Yield: 16.0 mg, 38%). HRMS (ES$^+$) m/z Calcd for $C_{30}H_{36}N_6O_3$. +H [(M+H)$^+$]: 529.2922. Found: 529.2917.

Similarly, but replacing 4-cyclopentylamino-2-methylsulfanyl-pyrimidine-5-carbaldehyde with 4-cyclopropylamino-2-methylsulfanyl-pyrimidine-5-carbaldehyde in step 6, 8-cyclopropyl-6-{5-(5-isobutyl-[1,3,4]oxadiazol-2-yl)-2-methyl-phenyl}-2-(tetrahydro-pyran-4-ylamino)-8H-pyrido[2,3-d]pyrimidin-7-one was prepared. HRMS (ES$^+$) m/z Calcd for $C_{28}H_{32}N_6O_3$+H [(M+H)$^+$]: 501.2609. Found: 501.2603.

Similarly, but replacing isovaleric anhydride with acetic anhydride in step 3,8-Cyclopentyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one was prepared. HRMS (ES$^+$) m/z Calcd for $C_{27}H_{30}N_6O_3$. +H [(M+H)$^+$]: 487.2452. Found: 487.2448.

Similarly, but replacing isovaleric anhydride with acetic anhydride in step 3, and replacing 4-cyclopentylamino-2-methylsulfanyl-pyrimidine-5-carbaldehyde with 4-cyclopropylamino-2-methylsulfanyl-pyrimidine-5-carbaldehyde in step 6,8-cyclopropyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one was prepared. HRMS (ES$^+$) m/z Calcd for $C_{25}H_{26}N_6O_3$+H [(M+H)$^+$]: 459.2139. Found: 459.2133.

Similarly, but replacing isovaleric anhydride with trifluoroacetic anhydride in step 3, and replacing 4-cyclopentylamino-2-methylsulfanyl-pyrimidine-5-carbaldehyde with 4-cyclopropylamino-2-methylsulfanyl-pyrimidine-5-carbaldehyde in step 6,8-cyclopropyl-6-[2-methyl-5-(5-trifluoromethyl-[1,3,4]oxadiazol-2-yl)-phenyl]-2-(tetrahydro-pyran-4-ylamino)-8H-pyrido[2,3-d]pyrimidin-7-one was prepared. HRMS (ES$^+$) m/z Calcd for $C_{25}H_{23}F_3N_6O_3$+H [(M+H)$^+$]: 513.1857. Found: 513.1852.

Additional compounds prepared by the procedure of Example 7 are shown in Table 1.

Example 8 p38 MAP Kinase Assay

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Using the above procedure, the compounds of the invention were found to be inhibitors of p38 MAP kinase. For example, 6-[5-(1H-Imidazol-2-yl)-2-methyl-phenyl]-8-methyl-2-(tetrahydro-pyran-4-ylamino)-8H-pyrido[2,3-d]pyrimidin-7-one exhibited a p38 IC$_{50}$ (uM) of approximately 0.00066.

Example 9 c-Raf HTRF Assay with 6H-MEK as Substrate (Dose Response)

This assay utilizes 6H-MEK as the substrate. Upon c-Raf phosphorylation, phosphorylated 6H-MEK is detected with rabbit anti-phospho-MEK1/2, Eu-labeled anti-rabbit, and APC-labeled anti-6H antibodies.

| Reagents and Antibodies | |
|---|---|
| Enzyme: | cloned human c-Raf with EE-tag; phosphorylated (co-expressed with v-src-FLAG in baculovirus Hi5 cells), 0.2 mg/mL (2.74 μM assuming a molecular weight of 73 kD) stored at −15° C. |
| Substrate: | WT full-length 6H-MEK, 4.94 mg/mL (154.4 μM assuming a MW of 32 kD) stored at −15° C. |
| Antibodies: | Rabbit (α-P-(Ser 217/221)-MEK-1/2 Ab (from Cell Signaling, Cat. # 9121B, Lot 14); Eu-(α-rabbit IgG (from Wallac, Cat. # AD0083, Lot 318663, 710 ug/mL, 4.4 μM); (α-6H-SureLight-APC (from Martek, Cat. #AD0059H, Lot E012AB01, 3.03 μM). |

| Instruments | |
|---|---|
| Reader: | Envision from PerkinElmer, HTRF reading mode with 412 mirror |
| Assay Plate: | Matrix all-black polypropylene plates (Cat. # 4344) |
| Compound plates: | Weidman 384 polypropylene plates (REMP). |

Procedure
(1) Prepare Kinase Assay Buffer (KAB): 50 mM HEPES (HyClone) pH7, 10 mM MgCl$_2$, 1 mM DTT, 0.1 mM Na$_3$V$_2$O$_4$, and 0.3 mg/ml BSA.
(2) Prepare 6H-MEK (150 nM) in KAB. Add 12 μl/well to the assay plate.
(3) Prepare ATP (66 μM) in KAB.
(4) Dilute compounds to 2.4 mM and any positive controls to 480 μM in DMSO. Perform 10-point 3× dilution in DMSO. Withdraw 2.5 μl/well of DMSO solution and add to 27.5 l/well ATP solution in (3).
(5) Mix, then add 6 μl/well of solution in (4) to the assay plate for a DMSO concentration of 2.1% during MEK phosphorylation.
(6) Prepare c-Raf (12 nM) in KAB.
(7) Add 6 μl/well of KAB in columns 1-2 and 6 μl/well of c-Raf in columns 3-24.
(8) Incubate at 37° C. for 30 min.
(9) Prepare rabbit (α-P-(Ser 217/221)-MEK-1/2 Ab (1:240 from stock) in AB1:50 mM HEPES pH7, 0.2 mg/ml BSA, and 43 mM EDTA.
(10) To stop reaction, add 6 μl/well of solution from (9) to the assay plate and incubate at 37° C. for 30 min.
(11) Prepare Eu-(α-rabbit IgG (9 nM) and (α-6H-SureLight-APC (120 nM) in AB2: 50 mM HEPES pH7 and 0.2 mg/ml BSA.
(12) Add 6 μl/well of solution from (11) to the assay plate.
(13) For determining the spectrum cross talk factor, prepare 2 samples following steps (1) to (10). For the blank sample, add 6 μl/well of AB2. For the cross talk factor sample, add 6 μl/well of Eu-anti rabbit IgG (9 nM).

(14) Incubate at room temperature for 1.5 hours.

(15) Read HTRF signals at 615 nm and 665 nm on the Envision. Normalize HTRF signals after spectrum cross-talk correction.

Expression and Purification of c-Raf

N terminal EE-tagged c-Raf was expressed in High-5 cells. A five liter culture was co-transfected with virus for EE-c-Raf and FLAG-vSrc at a ratio of 1:2 and harvested after 48 hours. The cell pellet was lysed in TBS containing 5 mM EDTA, 50 mM KF, 20 mM Na pyrophosphate, 20 mM β-glycerolphosphate, 0.5 mM Na VO$_3$, 1% NP-40 (w/v) and Complete Protease Tablets. The lysate was centrifuged at 20,000×g for 1 hour. The supernatant was incubated with 8 ml of anti-EE tag-Protein G Sepharose for 2 hours at 4° C. The resin was then washed with 30 volumes of the above buffer. The c-Raf protein was eluted by incubation with the above buffer containing 100 mg/ml of EE peptide for 1 hour at 4° C. Protein was concentrated using an Amicon Stir Cell with an YM10 membrane. The concentrated protein was dialyzed against TBS containing 1 mM DTT and 30% Glycerol. Protein concentration was determined by the BioRad DC method.

Purification of 6H-MEK1 (62-393)

E. coli cells containing the plasmid for the expression of 6H-MEK1 (62-393) were grown in Rich Media and induced with 1 mM IPTG for 24 hours at 22° C. The cell pellet was resuspent in 50 mM potassium phosphate buffer, pH 8.0, 300 mM NaCl, 5 mM MgCl$_2$, 10 mM CHAPS, 2 mM TCEP, and Complete Protease Inhibitor Tablets. Cells were disrupted by sonication. The lysate was cleared by centrifugation at 13,000×g for 45 minutes. The supernatant was diluted 1:1 with 50 mM potassium phosphate buffer, pH 8.0, 10 mM imidazole, 4 mM TCEP, 300 mM NaCl, 10 mM CHAPS, 2 mM pyrrole-2-carboxylate, and 100 mM ZnCl$_2$, then incubated with TALON metal affinity resin for 1 hour at 4° C.

The resin was washed with 10 volumes of 50 mM potassium phosphate buffer, pH 8.0, 5 mM imidazole, 2 mM TCEP, 300 mM NaCl, 10 mM CHAPS, 1 mM pyrrole-2-carboxylate, and 50 mM ZnCl$_2$. Proteins were eluted by incubation with 5 volumes of 20 mM HEPES, pH 8.0, 100 mM EDTA, 2 mM TCEP, 10% v/v glycerol for 1 hour at 4° C. The eluted material was concentrated using Amicon Ultra 15 devices with 10 Kd MW cutoff membranes. The sample was then subjected to size exclusion chromatography on a Superdex 200 26/60 column. The 6H-MEK1 Peak was pooled and concentrated as above. Protein was determined by the BioRad method.

Using the above procedure, compounds of the invention were shown to inhibit c-Raf. For example, the compound 8-methyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one exhibited an IC$_{50}$ (uM) of approximately 0.19 using the above assay.

Example 10 b-Raf Wild-Type HTRF Assay with 6H-MEK as Substrate (Dose Response)

This assay utilizes 6H-MEK as the substrate. Upon b-Raf WT phosphorylation, phosphorylated 6H-MEK is detected with rabbit anti-phospho-MEK1/2, Eu-labeled anti-rabbit, and APC-labeled anti-6H antibodies.

| | Reagents and Instruments |
|---|---|
| Enzyme: | recombinant human b-Raf residues 416-end with N-terminal GST-tag from Upstate; (expressed by baculovirus in Sf21 insect cells), 0.26 mg/mL (3.87 μM assuming a molecular weight of 67.2 kD) Cat. #14-530M, Lot #25502AU, stored at −80° C. |
| Substrate: | WT full-length 6H-MEK from C. Belunis (May 26, 2004), 4.94 mg/mL (154.4 μM assuming a MW of 32 kD) stored at −15° C. |
| Antibodies: | Rabbit (α-P-(Ser 217/221)-MEK-1/2 Ab (from Cell Signaling, Cat. # 9121B, Lot 14); Eu-(α-rabbit IgG (from Wallac, Cat. # AD0083, Lot 318663, 710 ug/mL, 4.4 μM); (α-6H-SureLight-APC (from Martek, Cat. #AD0059H, Lot E012AB01, 3.03 μM). |
| Reader: | Envision from PerkinElmer, HTRF reading mode with 412 mirror |
| Assay Plate: | Matrix all-black polypropylene plates (Cat. # 4344) |
| Others: | Weidman 384 polypropylene plates (REMP) for compound plate. |

Assay Procedure:

(1) Prepare Kinase Assay Buffer (KAB): 50 mM HEPES (HyClone) pH7, 10 mM MgCl$_2$, 1 mM DTT, 0.1 mM Na$_3$V$_2$O$_4$, and 0.3 mg/ml BSA.

(2) Prepare 6H-MEK (150 nM) in KAB. Add 12 μl/well to the assay plate.

(3) Prepare ATP (66 μM) in KAB.

(4) Dilute compounds to 2.4 mM and any positive controls to 480 μM in DMSO. Perform 10-point 3× dilution in DMSO. Withdraw 2.5 μl/well of DMSO solution and add to 27.5 μl/well ATP solution in (3).

(5) Mix, then add 6 μl/well of solution in (4) to the assay plate for a DMSO concentration of 2.1% during MEK phosphorylation.

(6) Prepare b-Raf WT (100 pM) in KAB.

(7) Add 6 μl/well of KAB in columns 1-2 and 6 μl/well of b-Raf WT in columns 3-24.

(8) Incubate at 37° C. for 30 min.

(9) Prepare rabbit (α-P-(Ser 217/221)-MEK-1/2 Ab (1:200 from stock) in AB1: 50 mM HEPES pH7, 0.2 mg/ml BSA, and 43 mM EDTA.

(10) To stop reaction, add 6 μl/well of solution from (9) to the assay plate and incubate at 37° C. for 30 min.

(11) Prepare Eu-(α-rabbit IgG (9 nM) and (α-6H-SureLight-APC (180 nM) in AB2:50 mM HEPES pH7 and 0.2 mg/ml BSA.

(12) Add 6 μl/well of solution from (11) to the assay plate.

(13) For determining the spectrum cross talk factor, prepare 2 samples following steps (1) to (10). For the blank sample, add 6 μl/well of AB2. For the cross talk factor sample, add 6 μl/well of Eu-anti rabbit IgG (9 nM).

(14) Incubate at room temperature for 1.5 hours.
(15) Read HTRF signals at 615 nm and 665 nm on the Envision. Normalize HTRF signals after spectrum cross-talk correction.

Using the above procedure, compounds of the invention were shown to inhibit wild type b-Raf. For example, the compound 4,N-dimethyl-3-[8-methyl-7-oxo-2-(tetrahydro-pyran-4-ylamino)-7,8-dihydro-pyrido[2,3-d]pyrimidin-6-yl]-benzamide exhibited an $IC_{50}$ (uM) of approximately 0.02 using the above assay.

Example 11 b-Raf V600E Mutant HTRF Assay with 6H-MEK as Substrate (Dose Response)

This assay utilizes 6H-MEK as the substrate. Upon b-Raf V600E phosphorylation, phosphorylated 6H-MEK is detected with rabbit anti-phospho-MEK1/2, Eu-labeled anti-rabbit, and APC-labeled anti-6H antibodies.

| Reagents and Instruments: | |
| --- | --- |
| Enzyme: | recombinant human b-Raf residues 416-end containing a V600E mutation with N-terminal GST-tag from Upstate; (expressed by baculovirus in Sf21 insect cells), 0.26 mg/mL (7.49 µM assuming a molecular weight of 67.3 kD) Cat. #14-5M, Lot #25633AU, stored at −80° C. |
| Substrate: | WT full-length 6H-MEK from C. Belunis (May 26, 2004), 4.94 mg/mL (154.4 µM assuming a MW of 32 kD) stored at −15° C. |
| Antibodies: | Rabbit (α-P-(Ser 217/221)-MEK-1/2 Ab (from Cell Signaling, Cat. # 9121B, Lot 14); Eu-(α-rabbit IgG (from Wallac, Cat. # AD0083, Lot 318663, 710 ug/mL, 4.4 µM); (α-6H-SureLight-APC (from Martek, Cat. #AD0059H, Lot E012AB01, 3.03 µM). |
| Reader: | Envision from PerkinElmer, HTRF reading mode with 412 mirror |
| Assay Plate: | Matrix all-black polypropylene plates (Cat. # 4344) |
| Others: | Weidman 384 polypropylene plates (REMP) for compound plate. |

Assay Procedure:
(1) Prepare Kinase Assay Buffer (KAB): 50 mM HEPES (HyClone) pH7, 10 mM $MgCl_2$, 1 mM DTT, 0.1 mM $Na_3V_2O_4$, and 0.3 mg/ml BSA.
(2) Prepare 6H-MEK (150 nM) in KAB. Add 12 µl/well to the assay plate.
(3) Prepare ATP (66 µM) in KAB.
(4) Dilute compounds to 2.4 mM and positive controls to 480 µM in DMSO. Perform 10-point 3× dilution in DMSO. Withdraw 2.5 µl/well of DMSO solution and add to 27.5 µl/well ATP solution in (3).
(5) Mix, then add 6 µl/well of solution in (4) to the assay plate for a DMSO concentration of 2.1% during MEK phosphorylation.
(6) Prepare b-Raf V600E (100 µM) in KAB.
(7) Add 6 µl/well of KAB in columns 1-2 and 6 µl/well of b-Raf V600E in columns 3-24.
(8) Incubate at 37° C. for 30 min.
(9) Prepare rabbit α-P-(Ser 217/221)-MEK-1/2 Ab (1:200 from stock) in AB1: 50 mM HEPES pH7, 0.2 mg/ml BSA, and 43 mM EDTA.
(10) To stop reaction, add 6 µl/well of solution from (9) to the assay plate and incubate at 37° C. for 30 min.
(11) Prepare Eu-α-rabbit IgG (9 nM) and α-6H-SureLight-APC (180 nM) in AB2: 50 mM HEPES pH7 and 0.2 mg/ml BSA.
(12) Add 6 µl/well of solution from (11) to the assay plate.
(13) For determining the spectrum cross talk factor, prepare 2 samples following steps (1) to (10). For the blank sample, add 6 µl/well of AB2. For the cross talk factor sample, add 6 µl/well of Eu-anti rabbit IgG (9 nM).
(14) Incubate at room temperature for 1.5 hours.
(15) Read HTRF signals at 615 nm and 665 nm on the Envision. Normalize HTRF signals after spectrum cross-talk correction.

Using the above procedure, compounds of the invention were shown to inhibit b-Raf V600E mutant. For example, the compound 4,N-dimethyl-3-[8-methyl-7-oxo-2-(tetrahydro-pyran-4-ylamino)-7,8-dihydro-pyrido[2,3-d]pyrimidin-6-yl]-benzamide exhibited an $IC_{50}$ (uM) of approximately 0.01 using the above assay.

Example 12

In Vitro Assay to Evaluate the Inhibition of LPS-induced TNF-α Production in THP1 Cells This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498-503 (1991).

(a) Induction of TNF Biosynthesis:

THP-1 cells were suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/mL and then plated in 96 well plate (0.2 mL aliquots in each well). Test compounds were dissolved in DMSO and then diluted with the culture medium such that the final DMSO concentration was 5%. Twenty five µL aliquots of test solution or only medium with DMSO (control) were added to each well. The cells were incubated for 30 min., at 37° C. LPS (Sigma, St. Louis, Mo.) was added to the wells at a final concentration of 0.5 µg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. GUT. Vol. 39(5), 684-689 (1996).

Polystyrene 96-well plates were coated with 50 µl per well of antibody 2TNF-H12 in PBS (10 µg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

Example 13

In Vitro Assay to Evaluate the Inhibition of LPS-induced TNF-α Production in THP1 Cells This example illustrates an in vivo assay to evaluate the inhibition of LPS-induced TNF-α production in mice (or rats).

The ability of the compounds of this invention to inhibit the TNF-α release, in vivo, was determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18-21 grams (Charles River, Hollister, Calif.) were acclimated for one week. Groups containing 8 mice each were dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

Example 14

Adjuvant-Induced Arthritis in Rats

AIA-induced arthritis is evaluated using the procedure of Badger et al., *Arthritis & Rheumatism*, 43(1) pp 175-183 (2000) AIA is induced by a single injection of 0.75 mg of parrafin-suspended *Mycobacterium Butycricum*) into male Lewis rats. Hindpaw volume is measured by water displacement on days 15, 20 and 30. A set of control animals is dosed with tragacanth. Test compounds in 0.5% tragacanth are administered orally at 3, 10, 30 and 60 mg/kg/day dosages. Indomethacin is used as a positive control. Percentage inhibition of hindpaw edema is calculated by 1-[AIA(treated)/AIA (control)]×100 where AIA (treated) and AIA (control) represent the mean paw volume.

Example 15

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

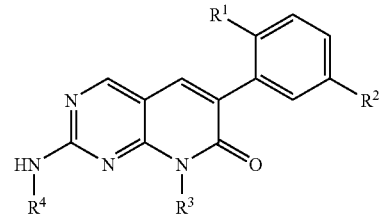

I or a pharmaceutically acceptable salt thereof,
wherein:
$R^1$ is:
  $C_{1-6}$alkyl;
  halo;
  $C_{1-6}$alkoxy;
  halo-$C_{1-6}$alkyl; or
  hetero-$C_{1-6}$alkyl;
$R^2$ is:
  cyano;
  an optionally substituted five membered monocyclic heteroaryl;
  —C(O)—$OR^a$;
  —C(O)—$NR^bR^c$; or
  —C(O)—$NR^d$—$NR^e$—$R^f$;
wherein
  $R^a$, $R^b$, $R^d$ and $R^e$ each independently is:
    hydrogen; or
    $C_{1-6}$alkyl; and
  $R^c$ and $R^f$ each independently is:
    hydrogen;
    $C_{1-6}$alkyl;
    halo-$C_{1-6}$alkyl;
    $C_{1-6}$alkoxy;
    hetero-$C_{1-6}$alkyl;
    $C_{3-6}$cycloalkyl;
    $C_{3-6}$cycloalkyl-$C_{1-6}$alkyl;
    aryl;
    aryl-$C_{1-6}$alkyl;
    heteroaryl; or
    heteroaryl-$C_{1-6}$alkyl;
    $C_{1-6}$alkyl-carbonyl;
    halo-$C_{1-6}$alkyl-carbonyl;
    aryl-carbonyl;
    aryl-$C_{1-6}$alkyl-carbonyl;
    heteroaryl-carbonyl; or
    heteroaryl-$C_{1-6}$alkyl-carbonyl.
$R^3$ is:
  $C_{1-6}$alkyl;
  $C_{3-6}$cycloalkyl;
  $C_{3-6}$cycloalkyl-$C_{1-6}$alkyl; or
  hetero-$C_{1-6}$alkyl; and
$R^4$ is:
  hetero-$C_{1-6}$alkyl; or
  heterocyclyl.

2. The compound of claim 1, wherein $R^3$ is $C_{1-6}$alkyl, $C_{3-6}$cycloalkyl or hetero-$C_{1-6}$alkyl.

3. The compound of claim 1, wherein $R^2$ is —C(O)—$NR^aR^b$, —C(O)—$NR^d$—$NR^e$—$R^f$; or an optionally substituted five membered monocyclic heteroaryl.

4. The compound of claim 1, wherein $R^2$ is oxazolyl, thiazolyl, isoxazolyl, isothiazolyl, imidazolyl, pyrazolyl, oxadiazolyl, thiadiazolyl or triazolyl, each optionally substituted.

5. The compound of claim 4, wherein $R^2$ is isoxazolyl, imidazolyl, oxadiazolyl or triazolyl, each optionally substituted.

6. The compound of claim 1, wherein $R^3$ is:
$C_{1-6}$alkyl selected from methyl, ethyl, propyl, isopropyl, n-butyl, isobutyl, tert-butyl, n-pentyl and isopentyl;
$C_{3-6}$cycloalkyl selected from cyclopropyl, cyclobutyl, cyclopentyl and cyclohexyl, each optionally substituted;
$C_{3-6}$cycloalkyl-$C_{1-6}$alkyl selected from cyclopropyl-$C_{1-6}$alkyl, cyclobutyl-$C_{1-6}$alkyl, cyclopentyl-$C_{1-6}$alkyl and cyclohexyl-$C_{1-6}$alkyl, the cycloalkyl portion of each being optionally substituted; or
hetero-$C_{1-6}$alkyl selected from $C_{1-6}$alkyloxy-$C_{1-6}$alkyl, hydroxy-$C_{1-6}$alkyl, $C_{1-6}$alkylsulfanyl-$C_{1-6}$alkyl, $C_{1-6}$alkyl-sulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl.

7. The compound of claim 1, wherein $R^4$ is:
hetero-$C_{1-6}$alkyl selected from $C_{1-6}$alkyloxy-$C_{1-6}$alkyl, hydroxy-$C_{1-6}$alkyl, $C_{1-6}$alkylsulfanyl-$C_{1-6}$alkyl, $C_{1-6}$alkyl-sulfinyl-$C_{1-6}$alkyl, $C_{1-6}$alkyl-sulfonyl-$C_{1-6}$alkyl, amino-$C_{1-6}$alkyl, N—$C_{1-6}$alkylamino-$C_{1-6}$alkyl, and N,N-di-$C_{1-6}$alkylamino-$C_{1-6}$alkyl or
heterocyclyl selected from piperidinyl, tetrahydropyranyl, pyrrolidinyl, tetrahydrofuranyl and tetrahydrothiopyranyl, each optionally substituted.

8. The compound of claim 7, wherein $R^4$ is heterocyclyl selected from piperidinyl, tetrahydropyranyl, pyrrolidinyl, tetrahydrofuranyl and tetrahydrothiopyranyl, each optionally substituted.

9. The compound of claim 1, wherein:
$R^1$ is methyl;
$R^2$ is:
an optionally substituted five membered monocyclic heteroaryl selected from oxazolyl thiazolyl, isoxazolyl, isothiazolyl, imidazolyl, pyrazolyl, oxadiazolyl, thiadiazolyl and triazolyl;
—C(O)—$NR^aR^b$, —C(O)—$NR^d$—$NR^e$—$R^f$; or —C(O)—$OR^a$, wherein $R^a$, $R^d$ and $R^e$ are hydrogen or $C_{1-6}$alkyl, and $R^b$ and $R^f$ are hydrogen, $C_{1-6}$alkyl, $C_{3-6}$cycloalkyl, $C_{3-6}$cycloalkyl-$C_{1-6}$alkyl aryl, aryl-$C_{1-6}$alkyl, halo-$C_{1-6}$alkyl or aryl-$C_{1-6}$alkyl-carbonyl or $C_{1-6}$alkoxy;
$R^3$ is methyl, cyclopropyl or cyclopentyl; and
$R^4$ is:
hydroxy-$C_{1-6}$alkyl;
$C_{1-6}$alkyl-sulfonyl-$C_{1-6}$alkyl; or
tetrahydropyran-4-yl.

10. The compound of claim 1, wherein:
$R^1$ is methyl;
$R^2$ is:
an optionally substituted five membered monocyclic heteroaryl selected from isoxazolyl, imidazolyl, oxadiazolyl and triazolyl; or
—C(O)—$NR^aR^b$ wherein $R^a$ is hydrogen or $C_{1-6}$alkyl, and $R^b$ is hydrogen, $C_{1-6}$alkyl, cyclopropyl or $C_{1-6}$alkoxy;
—C(O)—$NR^d$—$NR^e$—$R^f$ wherein $R^d$ and $R^e$ are hydrogen and $R^f$ is hydrogen, halo-$C_{1-6}$alkyl or aryl-$C_{1-6}$alkyl-carbonyl;
$R^3$ is methyl; and $R^4$ is:
hydroxy-$C_{1-6}$alkyl;
$C_{1-6}$alkyl-sulfonyl-$C_{1-6}$alkyl; or
tetrahydropyran-4-yl.

11. The compound of claim 1, wherein:
$R^1$ is methyl;
$R^2$ is an optionally substituted five membered monocyclic heteroaryl selected from isoxazolyl, imidazolyl, oxadiazolyl and triazolyl;
$R^3$ is methyl; and
$R^4$ is tetrahydropyran-1-yl.

12. A compound of the formula:

or a pharmaceutically acceptable salt thereof,
wherein $R^2$ is:
cyano;
an optionally substituted five membered monocyclic heteroaryl; —C(O)—$NR^aR^b$, —C(O)—$NR^d$—$NR^e$—$R^f$; or —C(O)—$OR^a$, wherein $R^a$, $R^d$ and $R^e$ are hydrogen or $C_{1-6}$alkyl, and $R^b$ and $R^f$ are hydrogen, $C_{1-6}$alkyl, $C_{3-6}$cycloalkyl, $C_{3-6}$cycloalkyl-$C_{1-6}$alkyl, aryl, aryl-$C_{1-6}$alkyl, halo-$C_{1-6}$alkyl or aryl-$C_{1-6}$alkyl-carbonyl or $C_{1-6}$alkoxy.

13. The compound of claim 12, wherein $R^2$ is an optionally substituted five membered monocyclic heteroaryl selected from oxazolyl, thiazolyl, isoxazolyl, isothiazolyl, imidazolyl, pyrazolyl, oxadiazolyl, thiadiazolyl and triazolyl.

14. The compound of claim 13, wherein $R^2$ is an optionally substituted five membered monocyclic heteroaryl selected from isoxazolyl, imidazolyl, oxadiazolyl and triazolyl.

15. A composition comprising:
(a) a pharmaceutically acceptable excipient; and
(b) a compound of claim 1.

16. The compound of claim 1, wherein said compound selected from the group consisting of:
4-Methyl-3-[8-methyl-7-oxo-2-(tetrahydro-pyran-4-ylamino)-7,8-dihydro-pyrido[2,3-d]pyrimidin-6-yl]-benzoic acid methyl ester;
N-Methoxy-4-methyl-3-[8-methyl-7-oxo-2-(tetrahydropyran-4-ylamino)-7,8-dihydro-pyrido[2,3-d]pyrimidin-6-yl]-benzamide;
6-[5-(5-Ethyl-[1,3,4]oxadiazol-2-yl)-2-methyl-phenyl]-8-methyl-2-(tetrahydro-pyran-4-ylamino)-8H-pyrido[2,3-d]pyrimidin-7-one;
8-Methyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one;
6-[5-(5-Ethyl-[1,3,4]oxadiazol-2-yl)-2-methyl-phenyl]-2-[3-hydroxy-1-(2-hydroxy-ethyl)-propylamino]-8-methyl-8H-pyrido[2,3-d]pyrimidin-7-one;
8-Methyl-6-(2-methyl-5-[1,3,4]oxadiazol-2-yl-phenyl)-2-(tetrahydro-pyran-4-ylamino)-8H-pyrido[2,3;

N-Cyclopropyl-4-methyl-3-[8-methyl-7-oxo-2-(tetrahydro-pyran-4-ylamino)-7,8-dihydro-pyrido[2,3-d]pyrimidin-6-yl]-benzamide;

4,N-Dimethyl-3-[8-methyl-7-oxo-2-(tetrahydro-pyran-4-ylamino)-7,8-dihydro-pyrido[2,3-d]pyrimidin-6-yl]-benzamide;

2-(2-Methanesulfonyl-1-methyl-ethylamino)-8-methyl-6-[2-methyl-5-(5-methyl-[1,3,4]oxadiazol-2-yl)-phenyl]-8H-pyrido[2,3-d]pyrimidin-7-one;

8-Methyl-6-[2-methyl-5-(3-methyl-isoxazol-5-yl)-phenyl]-2-(tetrahydro-pyran-4-ylamino)-8H-pyrido[2,3-d]pyrimidin-7-one;

8-Methyl-6-[2-methyl-5-(4H-[1,2,4]triazol-3-yl)-phenyl]-2-(tetrahydro-pyran-4-ylamino)-8H-pyrido[2,3-d]pyrimidin-7-one;

4-Methyl-3-[8-methyl-7-oxo-2-(tetrahydro-pyran-4-ylamino)-7,8-dihydro-pyrido [2,3-d]pyrimidin-6-yl]-benzonitrile;

6-[5-(1H-Imidazol-2-yl)-2-methyl-phenyl]-8-methyl-2-(tetrahydro-pyran-4-ylamino)-8H-pyrido[2,3-d]pyrimidin-7-one;

6-[5-(5-Isobutyl-[1,3,4]oxadiazol-2-yl)-2-methyl-phenyl]-8-methyl-2-(tetrahydro-pyran-4-ylamino)-8H-pyrido[2,3-d]pyrimidin-7-one;

6-{5-[5-(4-Chloro-phenyl)-[1,3,4]oxadiazol-2-yl]-2-methyl-phenyl}-8-methyl-2-(tetrahydro-pyran-4-ylamino)-8H-pyrido[2,3-d]pyrimidin-7-one;

6-{5-[5-(4-Chloro-benzyl)-[1,3,4]oxadiazol-2-yl]-2-methyl-phenyl}-8-methyl-2-(tetrahydro-pyran-4-ylamino)-8H-pyrido[2,3-d]pyrimidin-7-one;

8-Cyclopropyl-6-[5-(5-isobutyl-[1,3,4]oxadiazol-2-yl)-2-methyl-phenyl]-2-(tetrahydro-pyran-4-ylamino)-8H-pyrido[2,3-d]pyrimidin-7-one;

8-Cyclopentyl-6-[5-(5-isobutyl-[1,3,4]oxadiazol-2-yl)-2-methyl-phenyl]-2-(tetrahydro-pyran-4-ylamino)-8H-pyrido[2,3-d]pyrimidin-7-one;

8-Cyclopentyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one;

8-Cyclopropyl-6-[2-methyl-5-(5-methyl-[1,3,4]oxadiazol-2-yl)-phenyl]-2-(tetrahydro-pyran-4-ylamino)-8H-pyrido[2,3-d]pyrimidin-7-one;

8-Cyclopropyl-6-[2-methyl-5-(5-trifluoromethyl-[1,3,4]oxadiazol-2-yl)-phenyl]-2-(tetrahydro-pyran-4-ylamino)-8H-pyrido[2,3-d]pyrimidin-7-one;

6-[5-(5-Benzyl-[1,3,4]oxadiazol-2-yl)-2-methyl-phenyl]-8-methyl-2-(tetrahydro-pyran-4-ylamino)-8H-pyrido[2,3-d]pyrimidin-7-one;

8-Methyl-6-[2-methyl-5-(5-trifluoromethyl-[1,3,4]oxadiazol-2-yl)-phenyl]-2-(tetrahydro-pyran-4-ylamino)-8H-pyrido[2,3-d]pyrimidin-7-one;

6-{5-[5-(3-Chloro-benzyl)-[1,3,4]oxadiazol-2-yl]-2-methyl-phenyl}-8-methyl-2-(tetrahydro-pyran-4-ylamino)-8H-pyrido[2,3-d]pyrimidin-7-one;

4-Methyl-3-[8-methyl-7-oxo-2-(tetrahydro-pyran-4-ylamino)-7,8-dihydro-pyrido[2,3-d]pyrimidin-6-yl]-benzoic acid hydrazide;

4-Methyl-3-[8-methyl-7-oxo-2-(tetrahydro-pyran-4-ylamino)-7,8-dihydro-pyrido[2,3-d]pyrimidin-6-yl]-benzoic acid N'-(2,2,2-trifluoro-acetyl)-hydrazide;

4-Methyl-3-[8-methyl-7-oxo-2-(tetrahydro-pyran-4-ylamino)-7,8-dihydro-pyrido[2,3-d]pyrimidin-6-yl]-benzoic acid N'-phenylacetyl-hydrazide; and 4-Methyl-3-[8-methyl-7-oxo-2-(tetrahydro-pyran-4-ylamino)-7,8-dihydro-pyrido[2,3-d]pyrimidin-6-yl]-benzoic acid N'-[2-(3-chloro-phenyl)-acetyl]-hydrazide.

* * * * *